United States Patent
Dube et al.

(10) Patent No.: US 8,600,168 B2
(45) Date of Patent: Dec. 3, 2013

(54) METHODS AND SYSTEMS FOR IMAGE PROCESSING OF MICROFLUIDIC DEVICES

(75) Inventors: Simant Dube, Berkeley, CA (US); Gang Sun, Cupertino, CA (US); Lian-She Zhao, Fremont, CA (US)

(73) Assignee: Fluidigm Corporation, South San Francisco, CA (US)

( * ) Notice: Subject to any disclaimer, the term of this patent is extended or adjusted under 35 U.S.C. 154(b) by 94 days.

(21) Appl. No.: 13/253,857

(22) Filed: Oct. 5, 2011

(65) Prior Publication Data

US 2012/0245888 A1  Sep. 27, 2012

Related U.S. Application Data

(63) Continuation of application No. 11/900,927, filed on Sep. 13, 2007, now Pat. No. 8,055,034.

(60) Provisional application No. 60/844,465, filed on Sep. 13, 2006.

(51) Int. Cl.
*G06K 9/36* (2006.01)
*G06K 9/40* (2006.01)
*G06T 7/00* (2006.01)

(52) U.S. Cl.
CPC ............ *G06T 7/0012* (2013.01); *G06T 7/0044* (2013.01)
USPC ........... 382/190; 382/128; 382/133; 382/168; 382/170; 382/181

(58) Field of Classification Search
USPC ......... 382/128, 133, 168, 170, 181, 190, 195, 382/199, 206; 422/50, 504, 509; 435/5, 6, 435/86
See application file for complete search history.

(56) References Cited

U.S. PATENT DOCUMENTS 3,817,837 A  6/1974  Rubenstein et al.
3,850,752 A  11/1974  Schuurs et al.
(Continued)

FOREIGN PATENT DOCUMENTS

WO  WO 92/16657  10/1992
WO  WO 97/22719  6/1997
(Continued)

OTHER PUBLICATIONS

Guatelli et al., "Isothermal, in vitro amplification of nucleic acids by a multienzyme reaction modeled after retroviral replication," Proc. Nat. Acad. Sci. USA, 87:1874-1878 (1990).

(Continued)

*Primary Examiner* — David A Vanore
(74) *Attorney, Agent, or Firm* — Kilpatrick Townsend & Stockton LLP

(57) ABSTRACT

A method of processing data associated with fluorescent emissions from a microfluidic device. The method includes performing an auto-focus process associated with a first image of the microfluidic device and performing an auto-exposure process associated with the first image of the microfluidic device. The method also includes capturing a plurality of images of the microfluidic device. The plurality of images are associated with a plurality of thermal cycles. The method further includes performing image analysis of the plurality of captured images to determine a series of optical intensities and performing data analysis of the series of optical intensities to provide a series of change in threshold values.

15 Claims, 17 Drawing Sheets

(56) References Cited

U.S. PATENT DOCUMENTS

| | | | |
|---|---|---|---|
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 5,710,028 A | 1/1998 | Eyal et al. | |
| 5,723,591 A | 3/1998 | Livak et al. | |
| 5,846,710 A | 12/1998 | Bajaj | |
| 5,856,092 A | 1/1999 | Dale et al. | |
| 5,888,819 A | 3/1999 | Goelet et al. | |
| 5,945,283 A | 8/1999 | Kwok et al. | |
| 6,004,744 A | 12/1999 | Goelet et al. | |
| 6,540,895 B1 | 4/2003 | Spence et al. | |
| 6,706,471 B1 | 3/2004 | Brow et al. | |
| 6,716,620 B2* | 4/2004 | Bashir et al. | 435/287.2 |
| 6,727,071 B1* | 4/2004 | Dunlay et al. | 435/7.21 |
| 6,879,731 B2* | 4/2005 | Kang et al. | 382/274 |
| 6,885,982 B2 | 4/2005 | Harris et al. | |
| 6,902,883 B2* | 6/2005 | Dunlay et al. | 435/4 |
| 6,939,452 B2* | 9/2005 | Foret et al. | 204/458 |
| 6,951,632 B2 | 10/2005 | Unger et al. | |
| 6,995,847 B2* | 2/2006 | Fashant et al. | 356/445 |
| 7,010,174 B2* | 3/2006 | Kang et al. | 382/274 |
| 7,042,649 B2 | 5/2006 | Quake et al. | |
| 7,059,348 B2 | 6/2006 | Nat | |
| 7,062,418 B2 | 6/2006 | Lee et al. | |
| 7,097,809 B2 | 8/2006 | Dam et al. | |
| 7,161,736 B2 | 1/2007 | Legrand et al. | |
| 7,192,629 B2 | 3/2007 | Lammertink et al. | |
| 7,217,367 B2 | 5/2007 | Huang et al. | |
| 7,232,109 B2 | 6/2007 | Driggs et al. | |
| 7,239,757 B2* | 7/2007 | Kang et al. | 382/274 |
| 7,244,396 B2* | 7/2007 | Chait et al. | 422/501 |
| 7,247,274 B1* | 7/2007 | Chow | 422/504 |
| 7,248,413 B2 | 7/2007 | Quake et al. | |
| 7,262,923 B2 | 8/2007 | Quake et al. | |
| 7,279,146 B2 | 10/2007 | Nassef | |
| 7,291,512 B2 | 11/2007 | Unger | |
| 7,294,503 B2 | 11/2007 | Quake et al. | |
| 7,312,866 B2* | 12/2007 | Fashant et al. | 356/237.5 |
| 7,351,376 B1* | 4/2008 | Quake et al. | 422/504 |
| 7,368,163 B2 | 5/2008 | Huang et al. | |
| 7,382,931 B2* | 6/2008 | Kang et al. | 382/274 |
| 7,394,943 B2* | 7/2008 | Kinney et al. | 382/255 |
| 7,403,647 B2* | 7/2008 | Deutsch et al. | 382/133 |
| 7,442,556 B2 | 10/2008 | Manger et al. | |
| 7,476,363 B2 | 1/2009 | Unger et al. | |
| 7,509,038 B2* | 3/2009 | Poon et al. | 396/52 |
| 7,526,741 B2 | 4/2009 | Lee et al. | |
| 7,583,297 B2* | 9/2009 | Yamada | 348/224.1 |
| 7,583,853 B2* | 9/2009 | Taylor et al. | 382/276 |
| 7,604,965 B2 | 10/2009 | McBride et al. | |
| 7,616,791 B2* | 11/2009 | Soderman et al. | 382/128 |
| 7,659,968 B2* | 2/2010 | Wang et al. | 356/73 |
| 7,666,361 B2 | 2/2010 | McBride et al. | |
| 7,668,388 B2* | 2/2010 | Bryll | 382/255 |
| 7,678,547 B2 | 3/2010 | Eyal et al. | |
| 7,691,333 B2 | 4/2010 | McBride et al. | |
| 7,695,683 B2* | 4/2010 | Quan et al. | 422/504 |
| 7,738,695 B2* | 6/2010 | Shorte et al. | 382/154 |
| 7,749,737 B2 | 7/2010 | McBride et al. | |
| 7,792,345 B2* | 9/2010 | Taylor et al. | 382/128 |
| 7,815,868 B1 | 10/2010 | Jones et al. | |
| 7,820,427 B2 | 10/2010 | Unger et al. | |
| 7,833,708 B2 | 11/2010 | Enzelberger et al. | |
| 7,837,946 B2 | 11/2010 | McBride et al. | |
| 7,883,669 B2* | 2/2011 | Sun et al. | 422/504 |
| 7,911,617 B2* | 3/2011 | Padmanabhan et al. | 356/450 |
| 7,978,258 B2* | 7/2011 | Christiansen et al. | 348/364 |
| 8,009,206 B2* | 8/2011 | Masaki et al. | 348/241 |
| 8,050,516 B2* | 11/2011 | Dube et al. | 382/276 |
| 8,055,034 B2* | 11/2011 | Dube et al. | 382/128 |
| 2004/0180377 A1 | 9/2004 | Manger et al. | |
| 2005/0053952 A1 | 3/2005 | Hong et al. | |
| 2005/0205005 A1* | 9/2005 | Hansen et al. | 117/206 |
| 2005/0282175 A1 | 12/2005 | Taylor et al. | |
| 2006/0172408 A1 | 8/2006 | Quake et al. | |
| 2006/0233674 A1 | 10/2006 | Nelson | |
| 2006/0281183 A1* | 12/2006 | Sun et al. | 436/43 |
| 2007/0134807 A1 | 6/2007 | Bao et al. | |
| 2007/0224617 A1 | 9/2007 | Quake et al. | |
| 2007/0243523 A1* | 10/2007 | Ionescu-Zanetti et al. | 435/4 |
| 2007/0248971 A1 | 10/2007 | Maerkl et al. | |
| 2008/0050283 A1 | 2/2008 | Chou et al. | |
| 2008/0063251 A1* | 3/2008 | Deutsch | 382/133 |
| 2008/0075322 A1* | 3/2008 | Dube et al. | 382/100 |
| 2008/0075380 A1* | 3/2008 | Dube et al. | 382/255 |
| 2008/0108063 A1 | 5/2008 | Lucero et al. | |
| 2008/0129736 A1 | 6/2008 | Sun et al. | |
| 2008/0176211 A1 | 7/2008 | Spence et al. | |
| 2008/0176230 A1* | 7/2008 | Owen et al. | 435/6 |
| 2008/0223721 A1 | 9/2008 | Cohen et al. | |
| 2008/0230387 A1 | 9/2008 | McBride et al. | |
| 2008/0243523 A1 | 10/2008 | Beilis | |
| 2008/0264863 A1 | 10/2008 | Quake et al. | |
| 2008/0274493 A1 | 11/2008 | Quake et al. | |
| 2008/0281090 A1 | 11/2008 | Lee et al. | |
| 2008/0292504 A1 | 11/2008 | Goodsaid et al. | |
| 2009/0018195 A1 | 1/2009 | Balagadde | |
| 2009/0069194 A1 | 3/2009 | Ramakrishnan | |
| 2009/0074282 A1* | 3/2009 | Pinard et al. | 382/133 |
| 2009/0086046 A1* | 4/2009 | Reilly et al. | 348/222.1 |
| 2009/0142236 A1 | 6/2009 | Unger et al. | |
| 2009/0147918 A1 | 6/2009 | Fowler et al. | |
| 2009/0168066 A1 | 7/2009 | Hansen et al. | |
| 2009/0239308 A1 | 9/2009 | Dube et al. | |
| 2009/0262994 A1* | 10/2009 | Haussecker et al. | 382/128 |
| 2009/0291435 A1 | 11/2009 | Unger et al. | |
| 2010/0027857 A1* | 2/2010 | Wang | 382/128 |
| 2010/0104477 A1 | 4/2010 | Liu et al. | |
| 2010/0120018 A1 | 5/2010 | Quake et al. | |
| 2010/0120077 A1 | 5/2010 | Daridon | |
| 2010/0136549 A1* | 6/2010 | Christiansen et al. | 435/6 |
| 2010/0154890 A1 | 6/2010 | Maerkl et al. | |
| 2010/0166608 A1 | 7/2010 | Quan et al. | |
| 2010/0171954 A1 | 7/2010 | Quake et al. | |
| 2010/0183481 A1 | 7/2010 | Facer et al. | |
| 2010/0184202 A1 | 7/2010 | McBride et al. | |
| 2010/0187105 A1 | 7/2010 | Unger et al. | |
| 2010/0196892 A1 | 8/2010 | Quake et al. | |
| 2010/0197522 A1 | 8/2010 | Liu et al. | |
| 2010/0200782 A1 | 8/2010 | Unger et al. | |
| 2010/0230613 A1 | 9/2010 | Pieprzyk et al. | |
| 2010/0263732 A1 | 10/2010 | Hansen et al. | |
| 2010/0263757 A1 | 10/2010 | Fernandes et al. | |
| 2010/0311060 A1 | 12/2010 | Facer et al. | |
| 2010/0320364 A1 | 12/2010 | Unger et al. | |
| 2011/0115897 A1* | 5/2011 | Najmabadi et al. | 348/79 |
| 2011/0228993 A1* | 9/2011 | Reilly et al. | 382/128 |
| 2012/0176487 A1* | 7/2012 | Pinard et al. | 348/79 |
| 2012/0245888 A1* | 9/2012 | Dube et al. | 702/180 |
| 2013/0044222 A1* | 2/2013 | Tardif et al. | 348/187 |

FOREIGN PATENT DOCUMENTS

| | | |
|---|---|---|
| WO | WO 01/01025 A3 | 1/2001 |
| WO | WO 01/67369 A2 | 9/2001 |
| WO | WO 02/43615 | 6/2002 |
| WO | WO 2007/033385 A2 | 3/2007 |
| WO | WO 2007/044091 A2 | 4/2007 |
| WO | WO 2008/043046 A2 | 4/2008 |
| WO | WO 2009/100449 A1 | 8/2009 |
| WO | WO 2010/011852 A1 | 1/2010 |
| WO | WO 2010/017210 A1 | 2/2010 |
| WO | WO 2010/077618 A1 | 7/2010 |
| WO | WO 2011/053790 A2 | 5/2011 |

OTHER PUBLICATIONS

Kwoh et al., "Transcription-based amplification system and detection of amplified human immunodeficiency virus type 1 with a bead-based sandwich hybridization format,", Proc. Natl. Acad. Sci. USA 86:1173-1177 (1989).

(56) References Cited

OTHER PUBLICATIONS

Landegren et al., "A ligase-mediated gene detection technique.," Science 241:1077-1080 (1988).

Invader SNP assays, Proceedings-Spie the International Society for Optical Engineering, 3826:117-125, (2000).

Piatek et al., "Molecular beacon sequence analysis for detecting drug resistance in Mycobacterium tuberculosis," 1998, Nat. Biotechnol. 16:359-363.

Solinas et al., "Duplex Scorpion primers in SNP analysis and FRET applications" Nucleic Acids Research, 29(20):20 e96 (2001).

Sooknanan et al., "NASBA: A detection and amplification system uniquely suited for RNA," BioTechnology 13: 563-565 (Jun. 1995).

Thelwell et al. "Mode of action and application of Scorpion primers to mutation detection," Nucleic Acids Research, 28:3752-3761 (2000).

Tyagi et al, "Molecular Beacons: Probes that Fluoresce upon Hybridization," Nat. Biotechnology 14:303-308 (1996).

Tyagi, et al., "Multicolor Molecular Beacons for Allele Discrimination," Nat. Biotechnol. 16:49-53 (1998).

Unger, "Monolithic Microfabricated Valves and Pumps by Multilayer Soft Lithography," Science., 288(5463):113-6 (Apr. 7, 2000).

Wu et al., "The ligation amplification reaction (LAR)—amplification of specific DNA sequences using sequential rounds of template-dependent ligation.," Genomics 4(4):560-569 (1989).

Zhu et al., "High-Sensitivity Capillary Electrophoresis of Double-Stranded DNA Fragments Using Monomeric and Dimeric Fluorescent Intercalating Dyes," Anal. Chem. 66:1941-1948 (1994).

\* cited by examiner

METHODS AND SYSTEMS FOR IMAGE PROCESSING OF MICROFLUIDIC DEVICES

CROSS-REFERENCES TO RELATED APPLICATIONS

This application is a continuation of Ser. No. 11/900,927, filed Sep. 13, 2007; which claims benefit under 35 U.S.C. §119(e) of U.S. Provisional Patent Application No. 60/844,465, filed Sep. 13, 2006. U.S. patent application Ser. No. 11/900,927 was filed concurrently with U.S. patent application Ser. No. 11/900,926. The disclosures of these applications are hereby incorporated by reference in their entirety.

BACKGROUND OF THE INVENTION

The present invention relates generally to microfluidic techniques. In particular, the invention provides a method and system for imaging one or more entities suspended in a volume of fluid in a chamber of a microfluidic device. More particularly, the present method and system for imaging uses indications from a fluorescence signal associated with the one or more entities in the microfluidic device. Merely by way of example, the techniques for microfluidic methods and systems are applied using fluorescent, chemiluminescent, and bioluminescent readers coupled to the microfluidic device, but it would be recognized that the invention has a much broader range of applicability.

Concerted efforts to develop and manufacture microfluidic systems to perform various chemical and biochemical analyses and syntheses have occurred. Such systems have been developed for preparative and analytical applications. A goal to make such micro-sized devices arises from significant benefits achieved from miniaturization of conventional macro scale analyses and syntheses, which are often cumbersome and less efficient. A substantial reduction in time, lower costs, and more efficient space allocation are achieved as benefits using these microfluidic systems. Additional benefits may include a reduction in human operator involvement with automated systems using these microfluidic devices. Automated systems also decrease operator errors and other operator type limitations. Microfluidic devices have been proposed for use in a variety of applications, including, for instance, capillary electrophoresis, gas chromatography and cell separations.

Microfluidic devices adapted to conduct nucleic acid amplification processes are potentially useful in a wide variety of applications. For example, such devices could be used to determine the presence or absence of a particular target nucleic acid in a sample, as an analytical tool. Examples of utilizing microfluidic device as an analytical tool include:
- testing for the presence of particular pathogens (e.g., viruses, bacteria or fungi);
- identification processes (e.g., paternity and forensic applications);
- detecting and characterizing specific nucleic acids associated with particular diseases or genetic disorders;
- detecting gene expression profiles/sequences associated with particular drug behavior (e.g. for pharmacogenetics, i.e. choosing drugs which are compatible/especially efficacious for/not hazardous with specific genetic profiles); and
- conducting genotyping analyses and gene expression analyses (e.g., differential gene expression studies).

Alternatively, the devices can be used in a preparative fashion to amplify nucleic acids, producing an amplified product at sufficient levels needed for further analysis. Examples of these analysis processes include sequencing of the amplified product, cell-typing, DNA fingerprinting, and the like. Amplified products can also be used in various genetic engineering applications. These genetic engineering applications include (but are not limited to) the production of a desired protein product, accomplished by insertion of the amplified product into a vector that is then used to transform cells into the desired protein product.

Despite these potential applications, imaging systems (also referred to as readers) adapted to collect and process imaging data, for example, fluorescence data, from such microfluidic devices have various shortcomings related to the collection and processing of images. Therefore, there is a need in the art for improved methods and systems for imaging one or more entities suspended in a volume of fluid in a chamber of a microfluidic device.

SUMMARY OF THE INVENTION

According to the present invention, techniques for microfluidic systems are provided. In particular, the invention provides a method and system for imaging one or more entities suspended in a volume of fluid in a chamber of a microfluidic device. More particularly, the present method and system for imaging uses indications from a fluorescence signal associated with the one or more entities in the microfluidic device. Merely by way of example, the techniques for microfluidic methods and systems are applied using fluorescent, chemiluminescent, and bioluminescent readers coupled to the microfluidic device, but it would be recognized that the invention has a much broader range of applicability.

According to a specific embodiment according to the present invention, a method of processing data associated with fluorescent emissions from a microfluidic device is provided. The method includes performing an auto-focus process associated with a first image of the microfluidic device and performing an auto-exposure process associated with the first image of the microfluidic device. The method also includes capturing a plurality of images of the microfluidic device. The plurality of images are associated with a plurality of thermal cycles. The method further includes performing image analysis of the plurality of captured images to determine a series of optical intensities and performing data analysis of the series of optical intensities to provide a series of change in threshold values.

According to another embodiment of the present invention, a method of determining a focal plane for imaging a microfluidic device comprising a plurality of reaction chambers is provided. The method includes acquiring a stack of images. Each image in the stack of images is associated with a predetermined focal distance. The method also includes determining, for each image in the stack of images, a contrast score associated with each image and selecting a baseline image associated with a contrast score selected from the contrast scores associated with each image. The method further includes storing a focal distance associated with the baseline image and determining a plurality of positions associated with the plurality of reaction chambers. Each of the plurality of positions includes a number of chamber pixels. Moreover, the method includes determining, for each image in the stack of images, a contrast score associated with the plurality of positions associated with the plurality of reaction chambers and selecting an updated image associated with a contrast score selected from the contrast scores associated with the plurality of positions.

According to an alternative embodiment of the present invention, a method of performing an auto-focus process for a microfluidic device including a plurality of chambers is provided. The method includes acquiring an image stack comprising a plurality of images, determining a focal plane characterized by a predetermined contrast score, and determining a plurality of positions associated with the plurality of chambers. The method also includes computing a contrast score for each of the plurality of images in the image stack, determining an updated focal plane characterized by a second predetermined contrast score, and storing the updated focal plane in one or more memories.

According to another alternative embodiment of the present invention, a method of determining a baseline value associated with fluorescent emissions from a microfluidic device is provided. The method includes computing an initial baseline value, providing a first baseline value having a different value than the initial baseline value, and providing a series of emission data points as a function of PCR cycle number. The method also includes subtracting the initial baseline value from the series of emission data points to provide an initial baseline removed curve and computing an initial quality factor associated with initial baseline removed curve. The method further includes subtracting the first baseline value from the series of emission data points to provide a first baseline removed curve and computing a first quality factor associated with the first baseline removed curve. Moreover, the method includes determining that the first quality factor is greater than the second quality factor and determining that the baseline value is the first baseline value.

According to a specific embodiment of the present invention, a method of performing an auto-exposure process for an imaging system adapted to characterize a microfluidic device is provided. The method includes providing a histogram of pixel intensities, computing an average intensity for a range of pixels, and computing an exposure time. The method also includes computing a number of saturated pixels, and determining that the exposure time is less than a predetermined time and that the number of saturated pixels is less than a predetermined value.

According to another specific embodiment of the present invention, a method of determining a plurality of positions associated with a plurality of reaction chambers of a microfluidic device is provided. The method includes a) providing a baseline image, b) providing a template image of a reaction chamber, and c) selecting a region of the baseline image. The method also includes d) performing a matching process including matching the template image to one or more portions of the region of the baseline image, e) determining a position of a first chamber, and f) predicting a position of a second chamber. The method further includes g) repeating steps c) through f) for subsequent chambers.

According to yet another embodiment of the present invention, a method of removing a baseline from PCR ratio data is provided. The method includes obtaining a plurality of images. Each of the plurality of images is associated with a cycle of a PCR process. The method also includes determining a ratio of reporter dye to passive reference dye for each of the plurality of images, thereby providing a ratio data curve. The method further includes determining a corner point of the ratio data curve, determining a baseline value associated with the ratio data curve, and subtracting the baseline value from each value in the ratio data curve, thereby providing a baseline removed ratio data curve.

According to yet another specific embodiment of the present invention, a method for determining a ratio data value associated with a microfluidic device is provided. The method includes measuring a passive reference image for the microfluidic device. The passive reference image includes an array of reference intensity values. The method also includes measuring a reporter dye image for the microfluidic device. The reporter dye image includes an array of reporter intensity values. The method further includes determining a position of a reaction chamber of the microfluidic device, determining a low intensity value for the passive reference image in a vicinity of the position of the reaction chamber of the microfluidic device, and determining a low intensity value for the reporter dye image in a vicinity of the position of the reaction chamber of the microfluidic device. Additionally, the method includes subtracting the low intensity value for the passive reference image from the array of reference intensity values to provide a denominator value, subtracting the low intensity value for the reporter dye image from the array of reporter intensity values to provide a numerator value, and computing a ratio data value equal to the numerator value divided by the denominator value.

According to yet another alternative embodiment of the present invention, a method of determining a change in threshold value for a plurality of ratio data curves is provided. The method includes determining a first quality factor for a first ratio data curve of the plurality of ratio data curves, determining that the first quality factor is greater than a predetermined value, and determining a second quality factor for a second ratio data curve of the plurality of ratio data curves. The method also includes determining that the second quality factor is greater than the predetermined value and determining the change in threshold value based on the first ratio data curve and the second ratio data curve.

According to a particular embodiment of the present invention, a method of baseline correcting a ratio data curve associated with a PCR process for a microfluidic device is provided. The method includes providing a plurality of baseline values for the ratio data curve, computing a plurality of baseline removed curves, and computing a plurality of fitting errors for the plurality of baseline removed curves. The method also includes determining the minimum fitting error of the plurality of fitting errors, thereby determining a baseline value and computing the baseline corrected ratio data curve by removing the baseline value from the ratio data curve.

According to another specific embodiment of the present invention, a method of acquiring reporter images during a PCR process is provided. The method includes acquiring a passive reference image and determining an exposure time for the passive reference image. The method also includes determining a focal plane for the passive reference image and acquiring a plurality of reporter images at the determined focal plane using the determined exposure time.

According to yet another specific embodiment of the present invention, a method of determining a corner point for a PCR ratio data curve is provided. The method includes computing an estimate of a plurality of amplification factors. Each of the plurality of amplification factors is associated with a cycle of the PCR ratio data curve. The method also includes determining a maximum value of the plurality of amplification factors and identifying the cycle of the PCR ratio data curve associated with the maximum value as the corner point.

In an alternative embodiment of the present invention a method of determining a corner point for a PCR ratio data curve is provided. The method includes computing a plurality of derivative values. Each of the derivative values is associated with a cycle of the PCR ratio data curve. The method also includes determining a maximum value of the plurality of derivative values and identifying the cycle of the PCR ratio data curve associated with the maximum value as the corner point.

In yet another alternative embodiment of the present invention, a method of determining a corner point for a PCR ratio data curve is provided. The method includes a) computing an estimate of an amplification factor for a predetermined cycle number; b) determining a fitting window for the PCR ratio data curve, wherein the fitting window is associated with the predetermined cycle number; and c) fitting a first function to the PCR ratio data curve over the fitting window. The method also includes d) determining a fitting error for the first function; e) fitting a second function to the PCR ratio data curve over the fitting window; and f) determining a fitting error for the second function. The method further includes g) computing a difference between the fitting error for the first function and the fitting error for the second function, h) repeating steps a) through g) for subsequent cycle numbers; and i) identifying a maximum of the computed difference as the corner point.

Numerous benefits are achieved using the present invention over conventional techniques. Some embodiments provide optical imaging systems to generate and detect fluorescence from a microfluidic device. Additionally, embodiments of the present invention provide image processing systems that increase the detection sensitivity for fluorescent processes. Depending upon the embodiment, one or more of these benefits may exist. These and other benefits have been described throughout the present specification and more particularly below.

Various additional objects, features and advantages of the present invention can be more fully appreciated with reference to the detailed description and accompanying drawings that follow.

BRIEF DESCRIPTION OF THE DRAWINGS

FIG. 7D is a simplified plot of the derivative of RatioData as a function of PCR cycle number according to an embodiment of the present invention;

DETAILED DESCRIPTION OF SPECIFIC EMBODIMENTS

Figure 1A:
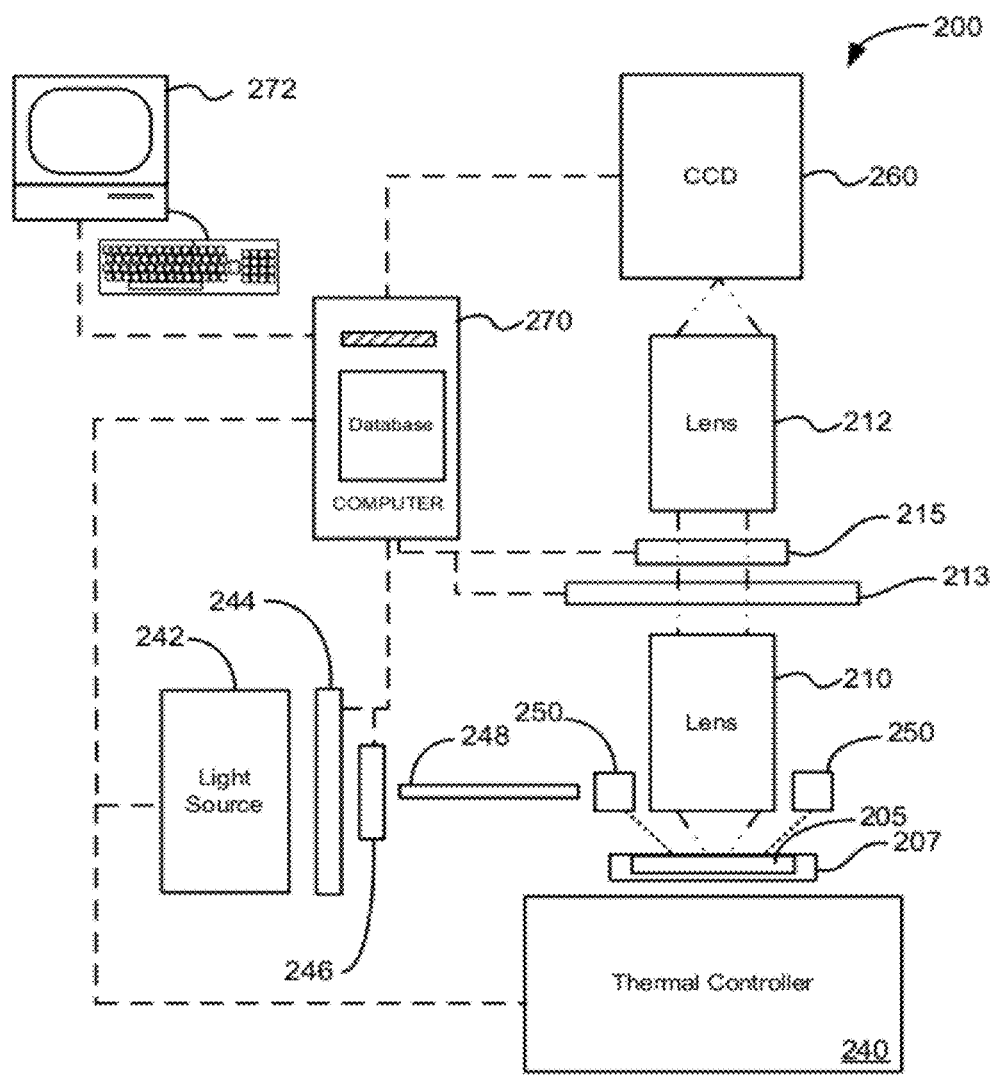
FIG. 1A is a simplified schematic diagram illustrating an optical imaging system according to an embodiment of the present invention.

According to the present invention, techniques for microfluidic systems are provided. In particular, the invention provides a method and system for imaging one or more entities suspended in a volume of fluid in a chamber of a microfluidic device. More particularly, the present method and system for imaging uses indications from a fluorescence signal associated with the one or more entities in the microfluidic device. Merely by way of example, the techniques for microfluidic methods and systems are applied using fluorescent, chemiluminescent, and bioluminescent readers coupled to the microfluidic device, but it would be recognized that the invention has a much broader range of applicability.

In some embodiments, a variety of devices and methods for conducting microfluidic analyses are utilized herein, including devices that can be utilized to conduct thermal cycling reactions such as nucleic acid amplification reactions. The devices differ from conventional microfluidic devices in that they include elastomeric components; in some instances, much or all of the device is composed of elastomeric material. For example, amplification reactions can be linear amplifications, (amplifications with a single primer), as well as exponential amplifications (i.e., amplifications conducted with a forward and reverse primer set).

The methods and systems provided by some embodiments of the present invention utilize blind channel type devices in performing nucleic acid amplification reactions. In these devices, the reagents that are typically deposited within the reaction sites are those reagents necessary to perform the desired type of amplification reaction. Usually this means that some or all of the following are deposited: primers, polymerase, nucleotides, metal ions, buffer, and cofactors, for example. The sample introduced into the reaction site in such cases is the nucleic acid template. Alternatively, however, the template can be deposited and the amplification reagents flowed into the reaction sites. As discussed in more detail throughout the present specification, when a matrix device is utilized to conduct an amplification reaction, samples containing nucleic acid template are flowed through the vertical flow channels and the amplification reagents through the horizontal flow channels or vice versa.

PCR is perhaps the best known amplification technique. The devices utilized in embodiments of the present invention are not limited to conducting PCR amplifications. Other types of amplification reactions that can be conducted include, but are not limited to, (i) ligase chain reaction (LCR) (see Wu and Wallace, *Genomics* 4:560 (1989) and Landegren et al., *Science* 241:1077 (1988)); (ii) transcription amplification (see Kwoh et al., *Proc. Natl. Acad. Sci. USA* 86:1173 (1989)); (iii) self-sustained sequence replication (see Guatelli et al., *Proc. Nat. Acad. Sci. USA,* 87:1874 (1990)); and (iv) nucleic acid based sequence amplification (NASBA) (see, Sooknanan, R. and Malek, L., *BioTechnology* 13: 563-65 (1995)). Each of the foregoing references are incorporated herein by reference in their entirety for all purposes.

Moreover, certain devices are designed to conduct thermal cycling reactions (e.g., PCR) with devices that include one or more elastomeric valves to regulate solution flow through the device. Thus, methods for conducting amplification reactions with devices of this design are also provided.

Amplicons can be detected and distinguished (whether isolated in a reaction chamber or at any subsequent time) using routine methods for detecting nucleic acids. Amplicons comprising double-stranded DNA can be detected using intercalation dyes such as SYBR™, Pico Green (Molecular Probes, Inc., Eugene, Oreg.), ethidium bromide and the like (see Zhu et al., 1994, Anal. Chem. 66:1941-48) and/or gel electrophoresis. More often, sequence-specific detection methods are used (i.e., amplicons are detected based on their nucleotide sequence). Examples of detection methods include hybridization to arrays of immobilized oligo or polynucleotides, and use of differentially labeled molecular beacons or other "fluorescence resonance energy transfer" (FRET)-based detection systems. FRET-based detection is a preferred method for detection according to some embodiments of the present invention. In FRET-based assays a change in fluorescence from a donor (reporter) and/or acceptor (quencher) fluorophore in a donor/acceptor fluorophore pair is detected. The donor and acceptor fluorophore pair are selected such that the emission spectrum of the donor overlaps the excitation spectrum of the acceptor. Thus, when the pair of fluorophores are brought within sufficiently close proximity to one another, energy transfer from the donor to the acceptor can occur and can be detected. A variety of assays are known including, for example and not limitation, template extension reactions, quantitative RT-PCR, Molecular Beacons, and Invader assays, these are described briefly below.

FRET and template extension reactions utilize a primer labeled with one member of a donor/acceptor pair and a nucleotide labeled with the other member of the donor/acceptor pair. Prior to incorporation of the labeled nucleotide into the primer during an template-dependent extension reaction, the donor and acceptor are spaced far enough apart that energy transfer cannot occur. However, if the labeled nucleotide is incorporated into the primer and the spacing is sufficiently close, then energy transfer occurs and can be detected. These methods are particularly useful in conducting single base pair extension reactions in the detection of single nucleotide polymorphisms and are described in U.S. Pat. No. 5,945,283 and PCT Publication WO 97/22719. The reactions can optionally be thermocycled to increase signal using the temperature control methods and apparatus described throughout the present specification.

A variety of so-called "real time amplification" methods or "real time quantitative PCR" methods can also be used to determine the quantity of a target nucleic acid present in a sample by measuring the amount of amplification product formed during or after the amplification process itself. Fluorogenic nuclease assays are one specific example of a real time quantitation method which can be used successfully with the devices described herein. This method of monitoring the formation of amplification product involves the continuous measurement of PCR product accumulation using a dual-labeled fluorogenic oligonucleotide probe—an approach frequently referred to in the literature as the "TaqMan" method. See, for example, U.S. Pat. No. 5,723,591.

With molecular beacons, a change in conformation of the probe as it hybridizes to a complementary region of the amplified product results in the formation of a detectable signal. The probe itself includes two sections: one section at the 5' end and the other section at the 3' end. These sections flank the section of the probe that anneals to the probe binding site and are complementary to one another. One end section is typically attached to a reporter dye and the other end section is usually attached to a quencher dye. In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. Probes of this type and methods of their use are described further, for example, by Piatek et al., 1998, Nat. Biotechnol. 16:359-63; Tyagi, and Kramer, 1996, Nat. Biotechnology 14:303-308; and Tyagi, et al., 1998, Nat. Biotechnol. 16:49-53 (1998).

The Scorpion detection method is described, for example, by Thelwell et al. 2000, Nucleic Acids Research, 28:3752-3761 and Solinas et al., 2001, "Duplex Scorpion primers in SNP analysis and FRET applications" Nucleic Acids Research 29:20. Scorpion primers are fluorogenic PCR primers with a probe element attached at the 5'-end via a PCR stopper. They are used in real-time amplicon-specific detection of PCR products in homogeneous solution. Two different formats are possible, the 'stem-loop' format and the 'duplex' format. In both cases the probing mechanism is intramolecular. The basic elements of Scorpions in all formats are: (i) a PCR primer; (ii) a PCR stopper to prevent PCR read-through of the probe element; (iii) a specific probe sequence; and (iv) a fluorescence detection system containing at least one fluorophore and quencher. After PCR extension of the Scorpion primer, the resultant amplicon contains a sequence that is complementary to the probe, which is rendered single-stranded during the denaturation stage of each PCR cycle. On cooling, the probe is free to bind to this complementary sequence, producing an increase in fluorescence, as the quencher is no longer in the vicinity of the fluorophore. The PCR stopper prevents undesirable read-through of the probe by Taq DNA polymerase.

Invader assays (Third Wave Technologies, Madison, Wis.) are used particularly for SNP genotyping and utilize an oligonucleotide, designated the signal probe, that is complementary to the target nucleic acid (DNA or RNA) or polymorphism site. A second oligonucleotide, designated the Invader Oligo, contains the same 5' nucleotide sequence, but the 3' nucleotide sequence contains a nucleotide polymorphism. The Invader Oligo interferes with the binding of the signal probe to the target nucleic acid such that the 5' end of the signal probe forms a "flap" at the nucleotide containing the polymorphism. This complex is recognized by a structure specific endonuclease, called the Cleavase enzyme. Cleavase cleaves the 5' flap of the nucleotides. The released flap binds with a third probe bearing FRET labels, thereby forming another duplex structure recognized by the Cleavase enzyme.

This time the Cleavase enzyme cleaves a fluorophore away from a quencher and produces a fluorescent signal. For SNP genotyping, the signal probe will be designed to hybridize with either the reference (wild type) allele or the variant (mutant) allele. Unlike PCR, there is a linear amplification of signal with no amplification of the nucleic acid. Further details sufficient to guide one of ordinary skill in the art are provided by, for example, Neri, B. P., et al., Advances in Nucleic Acid and Protein Analysis 3826:117-125, 2000) and U.S. Pat. No. 6,706,471.

As described above, a variety of multiplex amplification systems can be used in conjunction with the present invention. In one type, several different targets can be detected simultaneously by using multiple differently labeled probes each of which is designed to hybridize only to a particular target. Since each probe has a different label, binding to each target to be detected based on the fluorescence signals. By judicious choice of the different labels that are utilized, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992).

As used herein, a "detectable label" has the ordinary meaning in the art and refers to an atom (e.g., radionuclide), molecule (e.g., fluorescein), or complex, that is or can be used to detect (e.g., due to a physical or chemical property), indicate the presence of a molecule or to enable binding of another molecule to which it is covalently bound or otherwise associated. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, biochemical, immunochemical, electrical, optical or chemical means. Labels useful in the present invention include biotin for staining with labeled streptavidin conjugate, magnetic beads (e.g., Dynabeads™), fluorescent dyes (e.g., fluorescein, Texas red, rhodamine, green fluorescent protein, enhanced green fluorescent protein, lissamine, phycoerythrin, Cy2, Cy3, Cy3.5, Cy5, Cy5.5, Cy7, FluorX [Amersham], SyBR Green I & II [Molecular Probes], and the like), radiolabels (e.g., $^3$H, $^{125}$I, $^{35}$S, $^{14}$C, or $^{32}$P), enzymes (e.g., hydrolases, particularly phosphatases such as alkaline phosphatase, esterases and glycosidases, or oxidoreductases, particularly peroxidases such as horse radish peroxidase, and others commonly used in ELISAs), substrates, cofactors, inhibitors, chemiluminescent groups, chromogenic agents, and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art. Thus, for example, radiolabels and chemiluminescent labels may be detected using photographic film or scintillation counters, fluorescent markers may be detected using a photodetector to detect emitted light (e.g., as in fluorescence-activated cell sorting). Enzymatic labels are typically detected by providing the enzyme with a substrate and detecting the reaction product produced by the action of the enzyme on the substrate, and colorimetric labels are detected by simply visualizing the colored label. Thus, a label is any composition detectable by spectroscopic, photochemical, biochemical, immunochemical, electrical, optical or chemical means. The label may be coupled directly or indirectly to the desired component of the assay according to methods well known in the art. Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal generating system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody. The molecules can also be conjugated directly to signal generating compounds, e.g., by conjugation with an enzyme or fluorophore. Means of detecting labels are well known to those of skill in the art. Thus, for example, where the label is a radioactive label, means for detection include a scintillation counter, photographic film as in autoradiography, or storage phosphor imaging. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Also, simple colorimetric labels may be detected by observing the color associated with the label. It will be appreciated that when pairs of fluorophores are used in an assay, it is often preferred that the they have distinct emission patterns (wavelengths) so that they can be easily distinguished.

Many diseases linked to genome modifications, either of the host organism or of infectious organisms, are the consequence of a change in a small number of nucleotides, frequently involving a change in a single nucleotide. Such single nucleotide changes are referred to as single nucleotide polymorphisms or simply SNPs, and the site at which the SNP occurs is typically referred to as a polymorphic site. The devices described herein can be utilized to determine the identify of a nucleotide present at such polymorphic sites. As an extension of this capability, the devices can be utilized in genotyping analyses. Genotyping involves the determination of whether a diploid organism (i.e., an organism with two copies of each gene) contains two copies of a reference allele (a reference-type homozygote), one copy each of the reference and a variant allele (i.e., a heterozygote), or contains two copies of the variant allele (i.e., a variant-type homozygote). When conducting a genotyping analysis, the methods of the invention can be utilized to interrogate a single variant site. However, as described further below in the section on multiplexing, the methods can also be used to determine the genotype of an individual in many different DNA loci, either on the same gene, different genes or combinations thereof.

Devices to be utilized for conducting genotyping analyses are designed to utilize reaction sites of appropriate size to ensure from a statistical standpoint that a copy of each of the two alleles for a diploid subject are present in the reaction site at a workable DNA concentrations. Otherwise, an analysis could yield results suggesting that a heterozygote is a homozygote simply because a copy of the second allele is not present at the reaction site. Table 1 below indicates the number of copies of the genome present in a 1 nl reaction volume at various exemplary DNA concentrations that can be utilized with the devices described herein.

TABLE 1

Number of genome copies present in a 1 nanoliter volume at the indicated DNA concentration.

| Volume (nanoliter) | [DNA] (µg/µL) | N |
|---|---|---|
| 1 | 0.33 | 100 |
| 1 | 0.10 | 32 |
| 1 | 0.05 | 16 |
| 1 | 0.01 | 3 |
| 1 | 0.003 | 1 |

As a general matter, due to stochastic proportioning of the sample, the copy number present before an amplification reaction is commenced determines the likely error in the measurement. Genotyping analyses using certain devices are typically conducted with samples having a DNA concentration of approximately 0.10 µg/µL, although the current inventors have run successful TaqMan reactions at concentrations in which there is a single genome per reaction site.

Genotyping analyses can be conducted using a variety of different approaches. In these methods, it is generally sufficient to obtain a "yes" or "no" result, i.e., detection need only be able to answer the question whether a given allele is present. Thus, analyses can be conducted only with the primers or nucleotides necessary to detect the presence of one allele potentially at a polymorphic site. However, more typically, primers and nucleotides to detect the presence of each allele potentially at the polymorphic site are included.

Single Base Pair Extension (SBPE) reactions are one technique specifically developed for conducting genotyping analyses. Although a number of SPBE assays have been developed, the general approach is quite similar. Typically, these assays involve hybridizing a primer that is complementary to a target nucleic acid such that the 3' end of the primer is immediately 5' of the variant site or is adjacent thereto. Extension is conducted in the presence of one or more labeled non-extendible nucleotides that are complementary to the nucleotide(s) that occupy the variant site and a polymerase. The non-extendible nucleotide is a nucleotide analog that prevents further extension by the polymerase once incorporated into the primer. If the added non-extendible nucleotide(s) is(are) complementary to the nucleotide at the variant site, then a labeled non-extendible nucleotide is incorporated onto the 3' end of the primer to generate a labeled extension product. Hence, extended primers provide an indication of which nucleotide is present at the variant site of a target nucleic acid. Such methods and related methods are discussed, for example, in U.S. Pat. Nos. 5,846,710; 6,004, 744; 5,888,819; 5,856,092; and 5,710,028; and in WO 92/16657.

Genotyping analyses can also be conducted using quantitative PCR methods. In this case, differentially labeled probes complementary to each of the allelic forms are included as reagents, together with primers, nucleotides and polymerase. However, reactions can be conducted with only a single probe, although this can create ambiguity as to whether lack of signal is due to absence of a particular allele or simply a failed reaction. For the typical biallelic case in which two alleles are possible for a polymorphic site, two differentially labeled probes, each perfectly complementary to one of the alleles are usually included in the reagent mixture, together with amplification primers, nucleotides and polymerase. Sample containing the target DNA is introduced into the reaction site. If the allele to which a probe is complementary is present in the target DNA, then amplification occurs, thereby resulting in a detectable signal as described in the detection above. Based upon which of the differential signal is obtained, the identity of the nucleotide at the polymorphic site can be determined. If both signals are detected, then both alleles are present. Thermocycling during the reaction is performed as described in the temperature control section supra.

Gene expression analysis involves determining the level at which one or more genes is expressed in a particular cell. The determination can be qualitative, but generally is quantitative. In a differential gene expression analysis, the levels of the gene(s) in one cell (e.g., a test cell) are compared to the expression levels of the same genes in another cell (control cell). A wide variety of such comparisons can be made. Examples include, but are not limited to, a comparison between healthy and diseased cells, between cells from an individual treated with one drug and cells from another untreated individual, between cells exposed to a particular toxicant and cells not exposed, and so on. Genes whose expression levels vary between the test and control cells can serve as markers and/or targets for therapy. For example, if a certain group of genes is found to be up-regulated in diseased cells rather than healthy cells, such genes can serve as markers of the disease and can potentially be utilized as the basis for diagnostic tests. These genes could also be targets. A strategy for treating the disease might include procedures that result in a reduction of expression of the up-regulated genes.

The design of the microfluidic devices utilized in embodiments of the present invention is helpful in facilitating a variety of gene expression analyses. Because the devices contain a large number of reaction sites, a large number of genes and/or samples can be tested at the same time. Using the blind flow channel devices, for instance, the expression levels of hundreds or thousands of genes can be determined at the same time. The devices also facilitate differential gene expression analyses. With the matrix design, for example, a sample obtained from a healthy cell can be tested in one flow channel, with a sample from a diseased cell run in an immediately adjacent channel. This feature enhances the ease of detection and the accuracy of the results because the two samples are run on the same device at the same time and under the same conditions.

A variety of matrix or array-based devices are also utilized according to embodiments of the present invention. Certain of these devices include: (i) a first plurality of flow channels formed in an elastomeric substrate, (ii) a second plurality of flow channels formed in the elastomeric substrate that intersect the first plurality of flow channels to define an array of reaction sites, (iii) a plurality of isolation valves disposed within the first and second plurality of flow channels that can be actuated to isolate solution within each of the reaction sites from solution at other reaction sites, and (iv) a plurality of guard channels overlaying one or more of the flow channels and/or one or more of the reaction sites to prevent evaporation of solution therefrom. The foregoing devices can be utilized to conduct a number of different types of reactions, including those involving temperature regulation (e.g., thermocycling of nucleic acid analyses).

Some of the microfluidic devices utilize a design typically referred to herein as "blind channel" or "blind fill" and are characterized in part by having a plurality of blind channels, which are flow channels having a dead end or isolated end such that solution can only enter and exit the blind channel at one end (i.e., there is not a separate inlet and outlet for the blind channel). These devices require only a single valve for each blind channel to isolate a region of the blind channel to form an isolated reaction site. During manufacture of this type of device, one or more reagents for conducting an analysis are deposited at the reaction sites, thereby resulting in a significant reduction in the number of input and outputs. Additionally, the blind channels are connected to an interconnected network of channels such that all the reaction sites can be filled from a single, or limited number, of sample inputs. Because of the reduction in complexity in inputs and outputs and the use of only a single valve to isolate each reaction site, the space available for reaction sites is increased. Thus, the features of these devices means that each device can include a large number of reaction sites (e.g., up to tens of thousands) and can achieve high reaction site densities (e.g., over 1,000-4,000 reaction sites/cm$^2$). Individually and collectively, these features also directly translate into a significant reduction in the size of these devices compared to traditional microfluidic devices.

Other microfluidic devices that are disclosed herein utilize a matrix design. In general, microfluidic devices of this type utilize a plurality of intersecting horizontal and vertical flow channels to define an array of reaction sites at the points of intersection. Thus, devices of this design also have an array or reaction sites; however, there is a larger number of sample inputs and corresponding outputs to accommodate the larger number of samples with this design. A valve system referred to as a switchable flow array architecture enables solution be flowed selectively through just the horizontal or flow channels, thus allowing for switchable isolation of various flow channels in the matrix. Hence, whereas the blind channel devices are designed to conduct a large number of analyses under different conditions with a limited number of samples, the matrix devices are constructed to analyze a large number of samples under a limited number of conditions. Still other devices are hybrids of these two general design types.

The microfluidic devices that are described herein are further characterized in part by utilizing various components such as flow channels, control channels, valves and/or pumps fabricated from elastomeric materials. In some instances, essentially the entire device is made of elastomeric materials. Consequently, such devices differ significantly in form and function from the majority of conventional microfluidic devices that are formed from plastics or silicon-based materials. The number of reaction chambers provided according to embodiments of the present invention The design of the devices enables them to be utilized in combination with a number of different heating systems. Thus, the devices are useful in conducting diverse analyses that require temperature control. Additionally, those microfluidic devices adapted for use in heating applications can incorporate a further design feature to minimize evaporation of sample from the reaction sites. Devices of this type in general include a number of guard channels and/or reservoirs or chambers formed within the elastomeric device through which water can be flowed to increase the water vapor pressure within the elastomeric material from which the device is formed, thereby reducing evaporation of sample material from the reaction sites.

In another embodiment, a temperature cycling device may be used to control the temperature of the microfluidic devices. Preferably, the microfluidic device would be adapted to make thermal contact with the microfluidic device. Where the microfluidic device is supported by a substrate material, such as a glass slide or the bottom of a carrier plate, such as a plastic carrier, a window may be formed in a region of the carrier or slide such that the microfluidic device, preferably a device having an elastomeric block, may directly contact the heating/cooling block of the temperature cycling device. In a preferred embodiment, the heating/cooling block has grooves therein in communication with a vacuum source for applying a suction force to the microfluidic device, preferably a portion adjacent to where the reactions are taking place. Alternatively, a rigid thermally conductive plate may be bonded to the microfluidic device that then mates with the heating and cooling block for efficient thermal conduction resulting.

The array format of certain of the devices means the devices can achieve high throughput. Collectively, the high throughput and temperature control capabilities make the devices useful for performing large numbers of nucleic acid amplifications (e.g., polymerase chain reaction (PCR)). Such reactions will be discussed at length herein as illustrative of the utility of the devices, especially of their use in any reaction requiring temperature control. However, it should be understood that the devices are not limited to these particular applications. The devices can be utilized in a wide variety of other types of analyses or reactions. Examples include analyses of protein-ligand interactions and interactions between cells and various compounds. Further examples are provided throughout the present specification.

The microfluidic devices disclosed herein are typically constructed at least in part from elastomeric materials and constructed by single and multilayer soft lithography (MSL) techniques and/or sacrificial-layer encapsulation methods (see, e.g., Unger et al. (2000) Science 288:113-116, and PCT Publication WO 01/01025, both of which are incorporated by reference herein in their entirety for all purposes). Utilizing such methods, microfluidic devices can be designed in which solution flow through flow channels of the device is controlled, at least in part, with one or more control channels that are separated from the flow channel by an elastomeric membrane or segment. This membrane or segment can be deflected into or retracted from the flow channel with which a control channel is associated by applying an actuation force to the control channels. By controlling the degree to which the membrane is deflected into or retracted out from the flow channel, solution flow can be slowed or entirely blocked through the flow channel. Using combinations of control and flow channels of this type, one can prepare a variety of different types of valves and pumps for regulating solution flow as described in extensive detail in Unger et al. (2000) Science 288:113-116, and PCT Publication WO/02/43615 and WO 01/01025.

The devices provided herein incorporate such pumps and/or valves to isolate selectively a reaction site at which reagents are allowed to react. Alternatively, devices without pumps and/or valves are utilized that use pressure driven flow or polymerization processes to close appropriate channels and thereby selectively isolate reaction sites. The reaction sites can be located at any of a number of different locations within the device. For example, in some matrix-type devices, the reaction site is located at the intersection of a set of flow channels. In blind channel devices, the reaction site is located at the end of the blind channel.

If the device is to be utilized in temperature control reactions (e.g., thermocycling reactions), then, as described in greater detail infra, the elastomeric device is typically fixed to a support (e.g., a glass slide). The resulting structure can then be placed on a temperature control plate, for example, to control the temperature at the various reaction sites. In the case of thermocycling reactions, the device can be placed on any of a number of thermocycling plates.

Because the devices are made of elastomeric materials that are relatively optically transparent, reactions can be readily monitored using a variety of different detection systems at essentially any location on the microfluidic device. Most typically, however, detection occurs at the reaction site itself (e.g., within a region that includes an intersection of flow channels or at the blind end of a flow channel). The fact that the device is manufactured from substantially transparent materials also means that certain detection systems can be utilized with the current devices that are not usable with traditional silicon-based microfluidic devices. Detection can be achieved using detectors that are incorporated into the device or that are separate from the device but aligned with the region of the device to be detected.

Devices utilizing the matrix design generally have a plurality of vertical and horizontal flow channels that intersect to form an array of junctions. Because a different sample and reagent (or set of reagents) can be introduced into each of the flow channels, a large number of samples can be tested against a relatively large number of reaction conditions in a high throughput format. Thus, for example, if a different sample is introduced into each of M different vertical flow channels and a different reagent (or set of reagents) is introduced into each of N horizontal flow channels, then M×N different reactions can be conducted at the same time. Typically, matrix devices include valves that allow for switchable isolation of the vertical and horizontal flow channels. Said differently, the valves are positioned to allow selective flow just through the vertical flow channels or just through the horizontal flow channels. Because devices of this type allow flexibility with respect to the selection of the type and number of samples, as well as the number and type of reagents, these devices are well-suited for conducting analyses in which one wants to screen a large number of samples against a relatively large number of reaction conditions. The matrix devices can optionally incorporate guard channels to help prevent evaporation of sample and reactants.

Some high-density matrix designs utilize fluid communication vias between layers of the microfluidic device to weave control lines and fluid lines through the device. For example, by having a fluid line in each layer of a two layer elastomeric block, higher density reaction cell arrangements are possible. As will be evident to one of skill in the art, multi-layer devices allow fluid lines to cross over or under each other without being in fluid communication. For example, in a particular design, a reagent fluid channel in a first layer is connected to a reagent fluid channel in a second layer through a via, while the second layer also has sample channels therein, the sample channels and the reagent channels terminating in sample and reagent chambers, respectively. The sample and reagent chambers are in fluid communication with each other through an interface channel that has an interface valve associated therewith to control fluid communication between each of the chambers of a reaction cell. In use, the interface is first closed, then reagent is introduced into the reagent channel from the reagent inlet and sample is introduced into the sample channel through the sample inlet. Containment valves are then closed to isolate each reaction cell from other reaction cells. Once the reaction cells are isolated, the interface valve is opened to cause the sample chamber and the reagent chamber to be in fluid communication with each other so that a desired reaction may take place. One of ordinary skill in the art would recognize many variations, modifications, and alternatives.

Accordingly, a particular design for a microfluidic device provides for a microfluidic device adapted to react M number of different samples with N number of different reagents comprising: a plurality of reaction cells, each reaction cell comprising a sample chamber and a reagent chamber, the sample chamber and the reagent chamber being in fluid communication through an interface channel having an interface valve associated therewith for controlling fluid communication between the sample chamber and the reagent chamber; a plurality of sample inlets each in fluid communication with the sample chambers; a plurality of reagent inlets each in fluid communication with the reagent chambers; wherein one of the sample inlets or reagent inlets is in fluid communication with one of the sample chambers or one of the reagent chambers, respectively, through a via. Certain embodiments include having the reaction cells be formed within an elastomeric block formed from a plurality of layers bonded together and the interface valve is a deflectable membrane; having the sample inlets be in communication with the sample chamber through a sample channel and the reagent inlet in fluid communication with the reagent chamber through a reagent channel, a portion of the sample channel and a portion of the reagent channel being oriented about parallel to each other and each having a containment valve associated therewith for controlling fluid communication therethrough; having the valve associated with the sample channel and the valve associated with the reagent channel in operable communication with each other through a common containment control channel; having the containment common control channel located along a line about normal to one of the sample channel or the reagent channel.

The microfluidic devices utilized in embodiments of the present invention may be further integrated into the carrier devices described in co-pending and commonly owned U.S. Patent Application No. 60/557,715 by Unger filed on Mar. 29, 2004, which is incorporated herein for all purposes. The carrier of Unger provides on-board continuous fluid pressure to maintain valve closure away from a source of fluid pressure, e.g., house air pressure. Unger further provides for an automated system for charging and actuating the valves of the present invention as described therein. An another preferred embodiment, the automated system for charging accumulators and actuating valves employs a device having a platen that mates against one or more surfaces of the microfluidic device, wherein the platen has at least two or more ports in fluid communication with a controlled vacuum or pressure source, and may include mechanical portions for manipulating portions of the microfluidic device, for example, but not limited to, check valves.

Another device utilized in embodiments of the present invention provides a carrier used as a substrate for stabilizing an elastomeric block. Preferably the carrier has one or more of the following features; a well or reservoir in fluid communication with the elastomeric block through at least one channel formed in or with the carrier; an accumulator in fluid communication with the elastomeric block through at least one channel formed in or with the carrier; and, a fluid port in fluid communication with the elastomeric block, wherein the fluid port is preferably accessible to an automated source of vacuum or pressure, such as the automated system described above, wherein the automated source further comprises a platen having a port that mates with the fluid port to form an isolated fluid connection between the automated system for applying fluid pressure or vacuum to the elastomeric block. In devices utilized in certain embodiments, the automated source can also make fluid communication with one or more accumulators associated with the carrier for charging and discharging pressure maintained in an accumulator. In certain embodiments, the carrier may further comprise a region located in an area of the carrier that contacts the microfluidic device, wherein the region is made from a material different from another portion of the carrier, the material of the region being selected for improved thermal conduction and distribution properties that are different from the other portion of the carrier. Preferred materials for improved thermal conduction and distribution include, but are not limited to silicon, preferably silicon that is highly polished, such as the type of silicon available in the semiconductor field as a polished wafer or a portion cut from the wafer, e.g., chip.

As described more fully below, embodiments of the present invention utilize a thermal source, for example, but not limited to a PCR thermocycler, which may have been modified from its original manufactured state. Generally the thermal source has a thermally regulated portion that can mate with a portion of the carrier, preferably the thermal conduction and distribution portion of the carrier, for providing thermal control to the elastomeric block through the thermal conduction and distribution portion of the carrier. In a preferred embodiment, thermal contact is improved by applying a source of vacuum to a one or more channels formed within the thermally regulated portion of the thermal source, wherein the channels are formed to contact a surface of the thermal conduction and distribution portion of the carrier to apply suction to and maintain the position of the thermal conduction and distribution portion of the carrier. In a preferred embodiment, the thermal conduction and distribution portion of the carrier is not in physical contact with the remainder of the carrier, but is associated with the remainder of the carrier and the elastomeric block by affixing the thermal conduction and distribution portion to the elastomeric block only and leaving a gap surrounding the edges of the thermal conduction and distribution portion to reduce parasitic thermal effects caused by the carrier. It should be understood that in many aspects of the invention described herein, the preferred elastomeric block could be replaced with any of the known microfluidic devices in the art not described herein, for example devices produced such as the GeneChip® by Affymetrix® of Santa Clara, Calif., USA, or by Caliper of Mountain View, Calif., USA. U.S. patents issued to Soane, Parce, Fodor, Wilding, Ekstrom, Quake, or Unger, describe microfluidic or mesoscale fluidic devices that can be substituted for the elastomeric block of the present invention to take advantage of the thermal advantages and improvements, e.g., suction positioning, reducing parasitic thermal transfer to other regions of the fluidic device, which are described above in the context of using an elastomeric block.

Utilizing systems and methods provided according to embodiments of the present invention, throughput increases are provided over 384 well systems. As an example, throughput increases of a factor of 4, 6, 12, and 24 and greater are provided in some embodiments. These throughput increases are provided while reducing the logistical friction of operations. Moreover the systems and methods of embodiments of the present invention enable multiple assays for multiple samples. For example, in a specific embodiment 96 samples and 96 assays are utilized to provide a total of 9,216 data points. In a particular example, the 96 assays are components of a TaqMan 5' Nuclease Assay.

Furthermore, embodiments of the present invention provide reduced reaction volumes. In embodiments of the present invention, reaction volumes ranging from 10 picoliters to 100 nanoliters are utilized. In some embodiments, reaction volumes greater than 100 nanoliters are utilized. Merely by way of example, in an embodiment, the methods and systems of the present invention are utilized with reaction volumes of 10 picoliters, 50 picoliters, 100 picoliters, 250 picoliters, 500 picoliters, and 1 nanoliter. In alternative embodiments, reaction volumes of 2 nanoliters, 5 nanoliters, 10 nanoliters, 20 nanoliters, 30 nanoliters, 40 nanoliters, 50 nanoliters, 75 nanoliters, and 100 nanoliters are utilized.

Depending on the geometry of the particular microfluidic device and the size of the microfluidic device and the arrangement of the fluid communication paths and processing site, embodiments of the present invention provide for a range of processing site (or reaction chamber) densities. In some embodiments, the methods and systems of the present invention are utilized with chamber densities ranging from about 100 chambers per $cm^2$ to about 1 million chambers per $cm^2$. Merely by way of example, microfluidic devices with chamber densities of 250, 1,000, 2,500, 10,000, 25,000, 100,000, and 250,000 chambers per $cm^2$ are utilized according to embodiments of the present invention. In some embodiments, chamber densities in excess of 1,000,000 chambers per $cm^2$ are utilized, although this is not required by the present invention.

Operating microfluidic devices with such small reaction volumes reduces reagent usage as well as sample usage. Moreover, some embodiments of the present invention provide methods and systems adapted to perform real-time detection, when used in combination with real-time quantitative PCR. Utilizing these systems and methods, six orders of linear dynamic range are provided for some applications as well as quantitative resolution high enough to allow for the detection of sub-nanoMolar fluorophore concentrations in 10 nanoliter volumes. One of ordinary skill in the art would recognize many variations, modifications, and alternatives.

Methods conducted with certain blind channel type devices involve providing a microfluidic device that comprises a flow channel formed within an elastomeric material; and a plurality of blind flow channels in fluid communication with the flow channel, with an end region of each blind flow channel defining a reaction site. At least one reagent is introduced into each of the reaction sites, and then a reaction is detected at one or more of the reaction sites. The method can optionally include heating the at least one reagent within the reaction site. Thus, for example, a method can involve introducing the components for a nucleic acid amplification reaction and then thermocycling the components to form amplified product. As more fully described below, an optical imaging system adapted to characterize reactions occurring in certain microfluidic devices is provided according to embodiments of the present invention.

As illustrated in FIG. 1A, optical imaging systems provided according to some embodiments of the present invention include fluorescence imaging systems coupled to thermal control modules. Such systems are adapted to collect data from microfluidic chips with N×M geometries. In some embodiments, N is equal to M. For example, embodiments of the present invention utilize microfluidic devices with 48×48 reaction chambers, 96×96 reaction chambers, and other geometries. In a particular embodiment, 96 samples and 96 reagents are utilized in a microfluidic device with a 96×96 reaction chamber geometry. As will be evident to one of skill in the art, the methods and systems provided according to embodiments of the present invention enable one platform to perform multiple applications.

FIG. 1A is a simplified schematic diagram illustrating an optical imaging system according to an embodiment of the present invention. As illustrated in FIG. 1A, an optical source 242 is provided according to embodiments of the present invention. As will be described more fully below, in some embodiments of the present invention, light from optical source 242 is utilized to induce fluorescence in a sample. In other embodiments, chemiluminescence is utilized as an indicator. Depending on the embodiment, system components will be added, removed, or used, as will be evident to one of skill in the art. In various embodiments, optical sources including light emitting diodes (LEDs), lasers, arc lamps, incandescent lamps, and the like are utilized. These sources may be polychromatic or monochromatic. In a particular embodiment, the optical source is characterized by a first spectral bandwidth. In a specific embodiment, the optical source is a white light source producing optical radiation over a spectral range from about 400 nm to about 700 nm. Merely by way of example, a Lambda LS 300 W Xenon Arc lamp, available from Sutter Instruments of Novato, Calif. is utilized as an optical source is some embodiments of the present invention. As will be evident to one of skill in the art, other optical sources characterized by larger or smaller spectral bandwidths are capable of being utilized in alternative embodiments.

Excitation filter wheel 244 is illustrated in FIG. 1A. In some embodiments, for example, those in which the optical source is polychromatic, the excitation filter wheel 244 is utilized to spectrally filter the light emitted by the optical source 242. Of course, multiple filters could also be used. As an example, in an embodiment, the excitation filter wheel provides a number of spectral filters each adapted to pass a predetermined wavelength range as appropriate for exciting specific fluorescence from a sample. As illustrated in FIG. 1A, the excitation filter wheel 244 is coupled to computer 270, providing for computer control of the filters. In a particular embodiment, the excitation filter wheel provides a number of spectral filters:

Filter 1: A filter with a center wavelength of 485 nm and a spectral bandwidth of 20 nm;

Filter 2: A filter with a center wavelength of 530 nm and a spectral bandwidth of 20 nm; and Filter 3: A filter with a center wavelength of 580 nm and a spectral bandwidth of 20 nm.

As will be evident to one of skill in the art, embodiments of the present invention are not limited to these particular spectral filters, but will utilize spectral filters adapted for fluorescence processes for particular samples. Moreover, although the previous discussion related to the use of a filter wheel, this is not required by the present invention. In alternative embodiments, spectral filters are provided in geometries other than a wheel. For example, spectral filters that drop into a filter holder, electro-optic filters, filters placed into the optical path by actuators, and the like are included according to embodiments of the present invention. Moreover, in other embodiments, the optical source is a tunable laser adapted to emit radiation at predetermined wavelengths suitable for excitation of fluorescence. One of ordinary skill in the art would recognize many variations, modifications, and alternatives.

As illustrated in FIG. 1A, excitation shutter 246 is provided according to embodiments of the present invention. The excitation shutter is operated under control of a computer 270 in some embodiments, to block/pass the optical signal generated by the optical source 242 and spectrally filtered by the excitation filter wheel 244. Depending on the application, the excitation source is blocked while samples are inserted and removed from the system as well as for calibration operations. In some embodiments, the excitation shutter is not utilized, for example, in embodiments utilizing laser sources, which provide alternative means to extinguish the optical source.

When the excitation shutter is operated in an open position, the optical excitation signal passes through a fiber bundle 248 and is directed so as to impinge on a microfluidic device 205 provided in chip carrier to a seven. Other embodiments of the present invention utilize quartz light guides, liquid light guides, other scrambling systems, and the like to increase illumination homogeneity. As illustrated in FIG. 1A, the excitation optical signal is directed, through reflection by optical illuminator 250, refraction, or combinations thereof, to impinge on a surface of the microfluidic device 205. As illustrated in FIG. 1A, illumination of the microfluidic device is via optical illuminator 250. In other embodiments illumination maybe coupled to the microfluidic device obliquely from one or more sides of device, via a ring light, or via a portion of the collection optical train (the optical path between the microfluidic device and the detector 260.

In some embodiments, the illumination of the microfluidic device with light produced by the excitation source is provided over a two-dimensional area of the sample. In these embodiments, a large field of view is provided, which enables the performance of fluorescence applications that involve imaging of time resolved chemical processes and reactions. As an example, fluorescent imaging of protein calorimetry and nucleic acid amplification processes are time resolved processes that benefit from embodiments of the present invention. In some of these processes, simultaneously excitation of the fluorescent samples provided in a number of reaction chambers and simultaneous collection of the fluorescent signals produced by the reactions occurring in the number of reaction chambers is desirable. In other processes, for instance, fluorescence lifetime imaging, a brief excitation pulse is followed by detection (and analysis) of the fluorescent signal as it decays in time from an initial level. One of ordinary skill in the art would recognize many variations, modifications, and alternatives.

As an example, nucleic acid amplification processes typically include the target DNA, a thermostable DNA polymerase, two oligonucleotide primers, deoxynucleotide triphosphates (dNTPs), a reaction buffer, and magnesium. Once assembled, the reaction is placed in a thermal cycler, an instrument that subjects the reaction to a series of different temperatures for varying amounts of time. This series of temperature and time adjustments is referred to as one cycle of amplification. Each cycle theoretically doubles the amount of targeted sequence (amplicon) in the reaction. Ten cycles theoretically multiply the amplicon by a factor of about one thousand; 20 cycles, by a factor of more than a million in a matter of hours. In some applications, it is desirable to acquire fluorescent imaging data from a large area (e.g., on the order of several $cm^2$) in a time period ranging from seconds to minutes.

In some embodiments of the present invention, the methods and systems provided by embodiments of the present invention facilitate image capture processes that are performed in a predetermined time period. Merely by way of example, in an embodiment of the present invention a method of imaging microfluidic devices is provided. The method includes capturing an image of a spatial region associated with at least a determined number of chambers of a microfluidic device using an image detection spatial region during a time frame of less than one minute, whereupon the capturing of the image of the spatial region is substantially free from a stitching and/or scanning process.

Embodiments of the present invention provide a variety of time frames for image capture, ranging from 1 millisecond to 1 minute. In some embodiments, time frames for image capture are greater than one minute. Depending on the emission properties associated with the processes performed in the chambers of the microfluidic device, the time frame for image capture will vary. For example, in an embodiment, the time frame is 10 ms, 50 ms, 100 ms, 250 ms, 500 ms, 750 ms, or 1 second. In other embodiments, the time frame is 2 seconds, 5 seconds, 10 seconds, 15 seconds, 20 seconds, 30 seconds, 40 seconds, 50 seconds, or 1 minute. Of course, the time frame will depend on the particular applications.

In some embodiments, the image capture process is performed in a synchronous manner, capturing an image of a determined number of chambers simultaneously. As an example, in an exemplary PCR process, the microfluidic device is maintained at a temperature of 90° C. for a time period of 15 seconds. Subsequently, the microfluidic device is maintained at a temperature of 60° C. for 45 seconds. The heating and cooling cycle is repeated at a one minute cycle period for a number of cycles. Utilizing embodiments of the present invention, images of a determined number of chambers present in the microfluidic device are acquired synchronously, while the chambers are maintained at a uniform temperate as a function of position. For example, a two-dimensional image of an entire microfluidic device may be acquired utilizing a 30 second exposure while the microfluidic device is maintained at the temperature of 60° C. One of skill in the art will appreciate the benefits provided by the present invention over raster scanning or stitching systems, in which images of chambers in a first portion (e.g., an upper left quadrant) of the microfluidic device are acquired prior to images of chambers in a second portion (e.g., a lower right quadrant) of the microfluidic device.

In other embodiments, multiple images are acquired of the determined number of chambers during a time frame of less than one minute. As an example of these embodiments, multiple images associated with multiple fluorophores are acquired in a particular embodiment. During the 45 second time period during which the microfluidic device is maintained at the temperature of 60° C., three consecutive images utilizing exposures of 15 seconds may be acquired for three different fluorophores, for example, Rox™, Vic®, and Fam™. Utilizing these multiple images, differential fluorescence ratios can be calculated and analyzed. Of course, depending on the strength of the fluorescent emissions, the exposure times for the various fluorophores may be modified as appropriate the particular application. In this way, embodiments of the present invention provide for imaging of a microfluidic device in multiple spectral bands while the microfluidic device is maintained a constant temperature. The constant temperature, as illustrated by the previous example, may be a portion of a PCR process including cyclical temperature processes.

Embodiments of the present invention provide methods and systems are also adapted to perform and analyze chemiluminescence processes. In some of these processes, reactions occur on a first time scale and an image of the chemiluminescence process is acquired on a second time scale. In a particular process, the second time scale is less than the first time scale. Thus, embodiments of the present invention are adapted to capture synchronous images of chemiluminescence processes when the samples in the reaction chambers of interest have been reacting for an equal amount of time. In some of these processes, temperature control, including temperature cycling of the samples is provided, whereas in other embodiments, the reaction chambers are maintained at a constant temperature.

As illustrated in FIG. 1A, a thermal controller, also referred to as a temperature controller, 240 is provided according to embodiments of the present invention. A number of different options of varying sophistication are available for controlling temperature within selected regions of the microfluidic device or the entire device. Thus, as used herein, the term temperature controller is meant broadly to refer to a device or element that can regulate temperature of the entire microfluidic device or within a portion of the microfluidic device (e.g., within a particular temperature region or at one or more junctions in a matrix of channels of a microfluidic device).

Figure 1B:
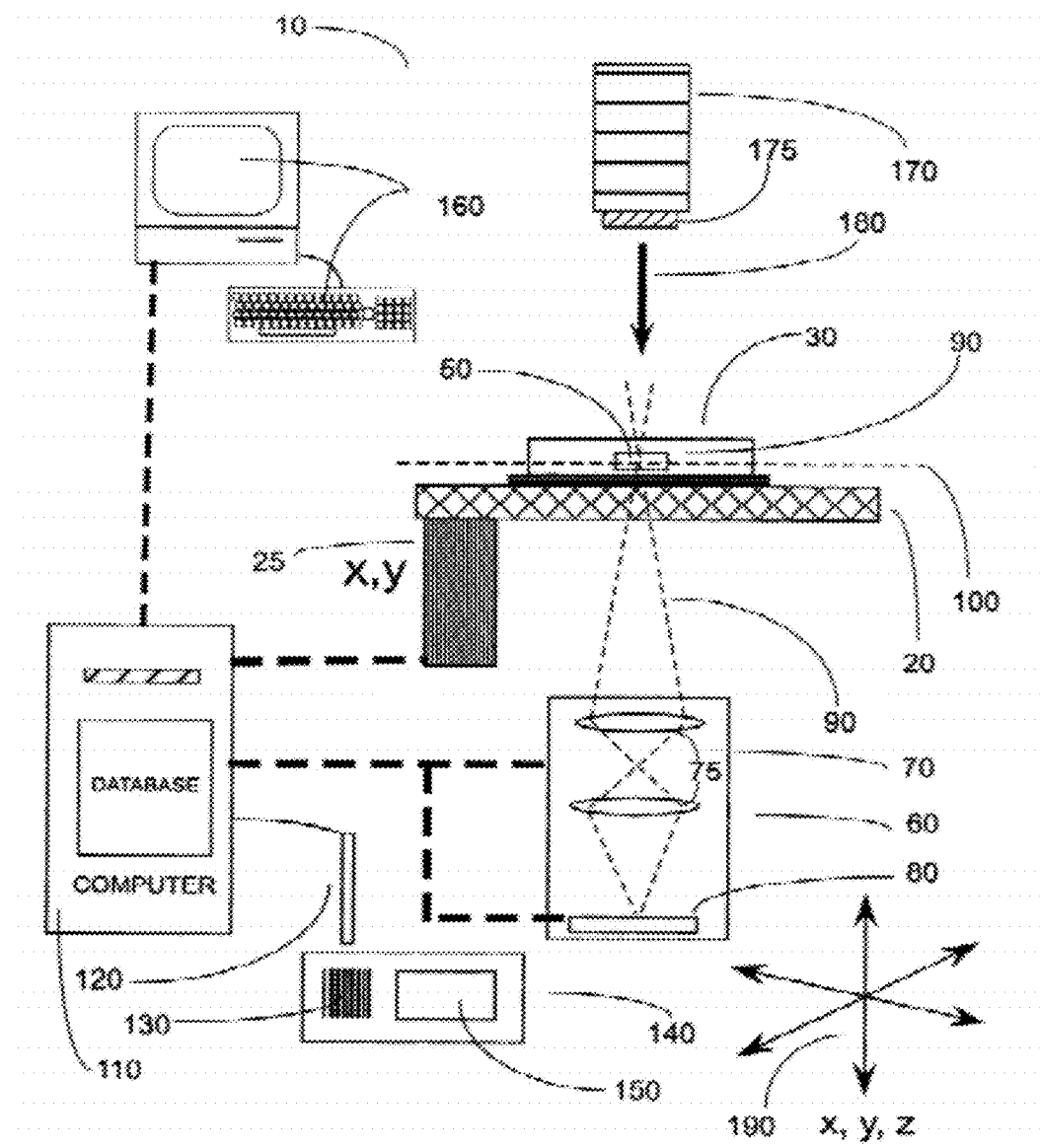
FIG. 1B depicts an overview of an exemplary imaging system according to an alternative embodiment of the present invention.
Figure 1C:
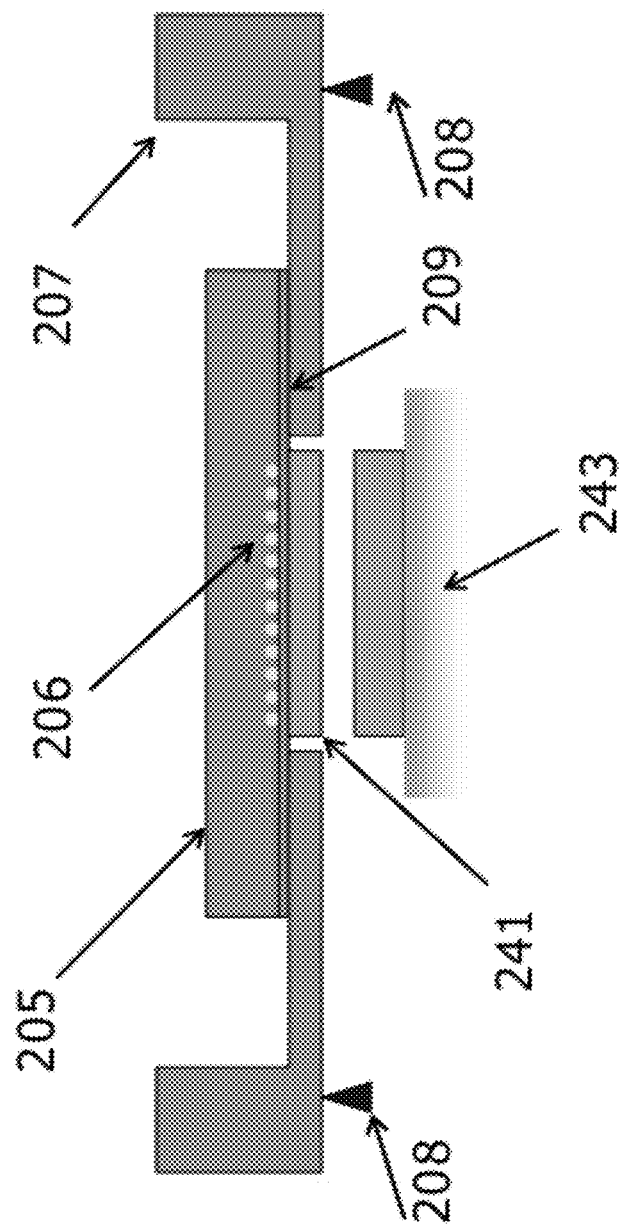
FIG. 1C is a simplified schematic diagram illustrating a thermal control device according to a embodiment of the present invention.

FIG. 1C is a simplified schematic diagram illustrating a thermal control device according to a embodiment of the present invention. As illustrated in FIG. 1C, microfluidic device 205 includes sample array 206. As will be evident to one of skill in the art, although the sample array 206 is illustrated in one dimension, three dimensional sample arrays are provided according to embodiments of the present invention. As an example, in some microfluidic devices utilized in embodiments of the present invention, an array of reaction chambers and fluid communication channels extend into the plane of the figure. The elements of the microfluidic device, including the reaction chambers are characterized by a depth in a third dimension. The microfluidic device 205 is supported by carrier 207, which, in turn, is supported by carrier supports 208. The microfluidic device or chip bottom layer 209, which in some embodiments is compliant, is coupled to the carrier 207 as well as the Integrated Heat Spreader (IHS) 241. Thermal platen 243 is illustrated in FIG. 1C and described more fully below. In some embodiments, a hard contact between the microfluidic device and the IHS/platen is provided. Moreover, as described in more detail below, vacuum techniques are utilized in some embodiments to position and hold the microfluidic device with respect to the carrier.

Generally, the devices are placed on a thermal cycling plate to thermal cycle the device. A variety of such plates are readily available from commercial sources, including for example the ThermoHybaid Px2 (Franklin, Mass.), MJ Research PTC-200 (South San Francisco, Calif.), Eppendorf Part# E5331 (Westbury, N.Y.), Techne Part#205330 (Princeton, N.J.).

In some embodiments, the microfluidic device is contacted with a thermal control device such that the thermal control device is in thermal communication with the thermal control source so that a temperature of the reaction in at least one of the reaction chamber is changed as a result of a change in temperature of the thermal control source. In different embodiments, the thermal transfer device may comprise a semiconductor, such as silicon, may comprise a reflective material, and/or may comprise a metal.

The thermal control device may be adapted to apply a force to the thermal transfer device to urge the thermal transfer device towards the thermal control source. The force may comprise a mechanical pressure, a magnetic force, an electrostatic force, or a vacuum force in different embodiments. For example, in one embodiment, the force comprises a vacuum force applied towards the thermal transfer device through channels formed in a surface of the thermal control device or the thermal transfer device. A level of vacuum achieved between the surface of the thermal control device and a surface (or a portion of a surface) of the thermal transfer device may be detected. Such detection may be performed with a vacuum level detector located at a position along the channel or channels distal from a location of a source of vacuum. When the vacuum does not exceed a preset level, an alert may be manifested or a realignment protocol may be engaged.

The array device may be contacted with the thermal control device by employment of one or more mechanical or electromechanical positioning devices. Carrying out of the method may be automatically controlled and monitored. For example, such automatic control and monitoring may be performed with an automatic control system in operable communication with a robotic control system for introducing and removing the array device from the thermal control device. The progress of the reactions may also be monitored.

A unit may be provided comprising the thermal control device. A system may be provided comprising the array device and the thermal control device. To ensure the accuracy of thermal cycling steps, in certain devices it is useful to incorporate sensors detecting temperature at various regions of the device. One structure for detecting temperature is a thermocouple. Such a thermocouple could be created as thin film wires patterned on the underlying substrate material, or as wires incorporated directly into the microfabricated elastomer material itself.

Temperature can also be sensed through a change in electrical resistance. For example, change in resistance of a thermistor fabricated on an underlying semiconductor substrate utilizing conventional techniques can be calibrated to a given temperature change. Alternatively, a thermistor could be inserted directly into the microfabricated elastomer material. Still another approach to detection of temperature by resistance is described in Wu et al. in "MEMS Flow Sensors for Nano-fluidic Applications", Sensors and Actuators A 89 152-158 (2001), which is hereby incorporated by reference in its entirety. This paper describes the use of doped polysilicon structures to both control and sense temperature. For polysilicon and other semiconductor materials, the temperature coefficient of resistance can be precisely controlled by the identity and amount of dopant, thereby optimizing performance of the sensor for a given application.

Thermo-chromatic materials are another type of structure available to detect temperature on regions of an amplification device. Specifically, certain materials dramatically and reproducibly change color as they pass through different temperatures. Such a material could be added to the solution as they pass through different temperatures. Thermo-chromatic materials could be formed on the underlying substrate or incorporated within the elastomer material. Alternatively, thermo-chromatic materials could be added to the sample solution in the form of particles.

Another approach to detecting temperature is through the use of an infrared camera. An infrared camera in conjunction with a microscope could be utilized to determine the temperature profile of the entire amplification structure. Permeability of the elastomer material to radiation of appropriate wavelengths (e.g. thermal, infrared, and the like) would facilitate this analysis.

Yet another approach to temperature detection is through the use of pyroelectric sensors. Specifically, some crystalline materials, particularly those materials also exhibiting piezoelectric behavior, exhibit the pyroelectric effect. This effect describes the phenomena by which the polarization of the material's crystal lattice, and hence the voltage across the material, is highly dependent upon temperature. Such materials could be incorporated onto the substrate or elastomer and utilized to detect temperature. Other electrical phenomena, such as capacitance and inductance, can be exploited to detect temperature in accordance with embodiments of the present invention. One of ordinary skill in the art would recognize many variations, modifications, and alternatives.

Imaging system 200 operates, in one embodiment, in the following manner. First, microfluidic device 205 is securely placed on carrier 207. Based on a fixed feature of the microfluidic device 205, for example, an edge of the base support of microfluidic device, computer 270 then causes and x,y drive (not shown) to move the carrier 207 to align the microfluidic device in a first x,y position. In some embodiments, one or more fiducial markings are utilized during the alignment and positioning process. In a specific embodiment, a user of the system then registers the precise coordinate of one or more fiducial marks with the imaging system. In other embodiments, this process is performed automatically as the centroids of the fiducials can be calculated precisely by locating a symmetric XY fiducial object and removing any non-symmetric components. In some embodiments, features of the fiducials, such as edges and corners are utilized during alignment processes. One of ordinary skill in the art would recognize many variations, modifications, and alternatives.

Under the control of computer 270, either adjustments of the carrier 207 to position it in the focal plane of the optical elements 210 and 212 or adjustments of the optical elements 210 and 212 to position the focal plane of the optical elements 210 and 212 to the carrier 207 are performed. In preferred embodiments, the field of view can embrace an entire microfluidic device, including the number of reaction chambers present on the microfluidic device.

A fluorescent, chemiluminescent, or optical signal emitted by the chemical processes occurring in the reaction chambers of the microfluidic device is collected by a first lens system 210. In some embodiments of the present invention, the first lens system is a multi-element optical train including one or more lenses and one or more apertures. As illustrated in FIG. 2A, first lens system 210 includes single lens elements as well as doublets, and the like. The optical properties of the first lens system 210 including focal length, f/#, and the like are selected to provide desired optical performance. One of ordinary skill in the art would recognize many variations, modifications, and alternatives. An emission shutter 215 is illustrated in FIG. 1A to provide for blocking of light rays propagating more than a predetermined distance from the optical axis, although this is not required by the present invention.

Referring once again to FIG. 1A, an optical filter device 213 is provided as part of the optical assembly. In some embodiments, the optical filter device is a filter wheel 213 comprising a number of optical elements adapted for passing and optically processing fluorescent or chemiluminescent emissions produced by fluorescently or chemiluminescently labeled reagents. As an example, in an embodiment, a first section of the emission filter wheel is adapted to pass fluorescent emissions produced by a first fluorescent dye, for example, Cy™3 Fluor, available from Amersham Biosciences, part of GE Healthcare of Piscataway, N.J. A second section of the emission filter wheel is adapted to pass fluorescent emissions produced by a second fluorescent dye, for example, Cy™5 Fluor also available from Amersham Biosciences. Of course, the use of these fluorescent dyes is not required by the present invention. In alternative embodiments, Alexa Fluors, available from Invitrogen Corporation of Carlsbad, Calif., are utilized. As an example, in another embodiment, a first section of the emission filter wheel is adapted to pass fluorescent emissions produced by a third fluorescent dye, for example, Alexa Fluor 350, available from Invitrogen Corporation. A second section of the emission filter wheel is adapted to pass fluorescent emissions produced by a fourth fluorescent dye, for example, Alexa Fluor 488, also available from Invitrogen Corporation. Additional details related to the emission filter wheel will be provided below.

In some embodiments, the optical filter device 213 and the emission shutter 215 are located between the first lens system and the second lens system. In some of these embodiments, light rays passing through the optical filter device propagate at small angles with respect to the optic axis. As will be evident to one of skill in the art, spectral filters (e.g., interference filters) placed in regions with small incident ray angle are simpler to design and can potentially provide narrower total spectral bandwidth, through such narrow spectral bandwidth characteristics and/or filter positioning are required by the present invention. As illustrated in FIG. 1A, both the optical filter device and the emission shutter are coupled to computer 270, providing for computer control of these elements. Moreover as will be evident to one of skill in the art, multiple, and possibly multiple identical filters, may be provided in the optical path to increase the blockage of excitation wavelengths. In some embodiments these filters are angled with respect to the optic axis so that light rays reflected off of the filters walk out of the optical path.

In other embodiments, certain intercalation dyes that have dramatic fluorescent enhancement upon binding to double-stranded DNA, and/or show strong chemical affinity for double-stranded DNA, can be used to detect double-stranded amplified DNA. Examples of suitable dyes include, but are not limited to, SYBR™ and Pico Green (from Molecular Probes, Inc. of Eugene, Oreg.), ethidium bromide, propidium iodide, chromomycin, acridine orange, Hoechst 33258, Toto-1, Yoyo-1, and DAPI (4',6-diamidino-2-phenylindole hydrochloride). Additional discussion regarding the use of intercalation dyes is provided by Zhu et al., *Anal. Chem.* 66:1941-1948 (1994), which is incorporated by reference in its entirety.

An second lens system 212 is also illustrated in FIG. 1A. Fluorescent or chemiluminescent emission passing through the optical filter device 213 and the emission shutter 215 is focused by the second lens system onto a detector 260. In an embodiment, the detector is a CCD camera array, but this is not required by the present invention. In a particular embodiment, an array detector, approximately the size of the microfluidic device, is utilized. Preferably, the pixel size of the detector array 260 is selected to provide an area smaller than the area of the reaction chambers in the microfluidic device, thereby providing multiple detector pixels per reaction chamber. In a particular embodiment, the detector 260 is a CCD array with approximately 15 µm×15 µm pixels.

A number of different detection strategies can be utilized with the microfluidic devices that are provided herein. Selection of the appropriate system is informed in part on the type of event and/or agent being detected. The detectors can be designed to detect a number of different signal types including, but not limited to, signals from radioisotopes, fluorophores, chromophores, electron dense particles, magnetic particles, spin labels, molecules that emit chemiluminescence, electrochemically active molecules, enzymes, cofactors, enzymes linked to nucleic acid probes and enzyme substrates.

Illustrative detection methodologies suitable for use with the present microfluidic devices include, but are not limited to, light scattering, multichannel fluorescence detection, UV and visible wavelength absorption, luminescence, differential reflectivity, and confocal laser scanning. Additional detection methods that can be used in certain application include scintillation proximity assay techniques, radiochemical detection, fluorescence polarization anisotropy, fluorescence lifetime, fluorescence correlation spectroscopy (FCS), time-resolved energy transfer (TRET), fluorescence resonance energy transfer (FRET) and variations such as bioluminescence resonance energy transfer (BRET). Additional detection options include electrical resistance, resistivity, impedance, and voltage sensing.

In some embodiments, detection occurs at a "detection section," or "detection region." These terms and other related terms refer to the portion of the microfluidic device at which detection occurs. In some microfluidic devices, the detection section is generally the reaction chambers present in the microfluidic device. The detection section for matrix-based devices is usually within regions of flow channels that are adjacent an intersection, the intersection itself, or a region that encompasses the intersection and a surrounding region.

The detection section can be in communication with one or more microscopes, diodes, light stimulating devices (e.g., lasers), photomultiplier tubes, processors and combinations of the foregoing, which cooperate to detect a signal associated with a particular event and/or agent. Often the signal being detected is an optical signal that is detected in the detection section by one or more optical detectors. The optical detector can include one or more photodiodes (e.g., avalanche photodiodes), a fiber-optic light guide leading, for example, to a photomultiplier tube or tubes, a microscope, and/or a video camera (e.g., a CCD camera).

Detectors can be microfabricated within the microfluidic device, or can be a separate element. If the detector exists as a separate element and the microfluidic device includes a plurality of detection sections, detection can occur within a single detection section at any given moment. As a specific illustrative example, the microfluidic device can be attached to a translatable stage and scanned under a microscope objective. A signal so acquired is then routed to a processor for signal interpretation and processing. Arrays of photomultiplier tubes can also be utilized. Additionally, optical systems that have the capability of collecting signals from all the different detection sections simultaneously while determining the signal from each section can be utilized.

External detectors are usable because the devices that are provided are completely or largely manufactured of materials that are optically transparent at the wavelength being monitored. This feature enables the devices described herein to utilize a number of optical detection systems that are not possible with conventional silicon-based microfluidic devices.

A particular embodiment of the present invention utilizes a detector in the form of a CCD camera and an optical path that provides for a large field of view and a high numerical aperture to maximize the amount of light collected from each reaction chamber, thereby increasing detection sensitivity. In this embodiment, the CCD is used as an array of photodetectors wherein each pixel or group of pixels corresponds to a reaction chamber rather than being used to produce an image of the array. Thus, the optics may be designed or altered such that image quality is reduced or the image is blurred at the detector in order to increase the useable depth of field of the optical system to collect more light from each reaction chamber. Particularly because the assays contemplated in some embodiments of the present invention include biological assays using fluorescent dyes, which dyes photobleach due to exposure to excitation light hence limiting the total number of signal photons obtainable from a given sample, efficient collection of the limited signal photons can be of importance in instruments such as that discussed. Etendue considerations relate the object and image NA (numerical aperture) and total system magnification for any optical system; since image-side NA can be limited (e.g. by reflection losses at the CCD surface for high-incident-angle rays), in general, arbitrarily high object (sample)-side NA is not achievable simultaneously with arbitrary system magnification. In fact, a larger system magnification can allow a higher object-side NA without requiring a simultaneous (and potentially deleterious for reasons described above) rise in image-side NA. Consequently, in the system described, a large CCD (e.g., 30.7 mm×30.7 mm) focal-plane array has been used to allow for a 1:1 optical system (i.e., a system magnification of 1). This allows a collection NA of 0.36 simultaneous with an image-side NA of 0.36 onto the CCD, which provides reasonable performance with respect to surface reflection losses.

In some embodiments, larger object-side NAs result in reduced object-side depth-of-focus, and hence larger blurring at the detector (assuming blur due to depth of focus greater than or equal to blur due to lens aberrations and other issues) for a given depth of reaction chamber in the sample, limiting the allowable minimum spacing between reaction chambers at the sample if low crosstalk in signal between chambers is to be achieved. In conjunction with a 1:1 optical system, this object-side NA consideration is in good keeping with the ~0.5 NA maximum generally desirable NA onto a CCD (or silicon detector) if one is to avoid reflection losses at the surface thereof. The 1:1 imaging lens system is furthermore inherently free of most odd-order aberrations, increasing the advantage of this particular magnification (M=1). The use of a 1:1 optical system with a detector as large or larger than the microfluidic system to be imaged is thus provided by some embodiments of the present invention as a design for the detailed system.

In other embodiments, there may be a cost constraint related to the size of the detector (e.g. a CCD focal-plane array). For example, some current high quantum-efficiency, full-frame CCD arrays have dimensions of 27.6 mm×27.6 mm. This detector is slightly smaller than a microfluidic device with dimensions of 30.7 mm×30.7 mm, resulting in a system magnification of 0.88 as a design for the system described. Being near system magnification M=1, constraints related to the detector (image-side) incident NA described above are satisfied for such a magnification.

In other embodiments, a given XY-plane (perpendicular to the optical axis) spacing and size of the reaction chambers may be specified (e.g. to achieve a desired density of sample-chambers in the XY-plane), while constraints on the minimum total volume of the chambers remain (e.g. to achieve minimum required chemical volumes, for instance to avoid over-large statistical fluctuations due to small numbers of reagent or target molecules, or simply to achieve a required minimum number of fluorescent or otherwise optically-emitting molecules or objects). In such a case, it may be necessary to extend the chambers parallel to the Z (optical)-axis such that the total volume of each chamber remains equal to or greater than some minimum figure. Greater extension along Z (creating high-aspect ratio, or columnar chambers which concentrate the sample to be interrogated along the Z-axis) will generally result in a larger blur of the chamber image at the detector for given object-side NA, due to depth-of-focus considerations, assuming blur due to depth of focus is greater than or equal to blur due to lens aberrations and other issues. In some situations, this will lead to the user of a lower object-side NA. Use of a lower NA lens system allows for greater depth of focus and hence light collection from a chambers extended parallel to the optic axis without generally incurring inordinate crosstalk in the optical signal between adjacent or nearby chambers. In this way, a greater density of chambers in the X-Y plane (the place perpendicular to the optic axis) may be used without inordinate crosstalk, while the total chamber volume may be kept large by extension of the chambers in Z (parallel to the optic axis). In this case, or other cases where a lower object-side NA is acceptable (e.g., cases where a larger XY spacing of reaction chambers allows for more chamber-image blur at the detector without undue crosstalk; in non-light-limited applications, where higher NA is not essential; where there is sufficient sample that photobleaching is not an issue; non-photobleaching samples, circumstances such as lower acceptable system sensitivity), a lower system magnification (M<1) may be suitable, particularly if $M \geq NA_o/0.5$, or more preferably $M \geq NA_o/0.36$, where $NA_o$=object side NA, or more generally $M \geq NA_o/NA_{det}$ where $NA_{det}$=maximum NA allowable onto the detector face without overlarge reflection/insertion losses to the detector ($NA_{det}$=0.36 to 0.5 for a typical CCD).

In cases where object-side depth-of-focus and/or blur requirements do not necessitate an object-side $NA \leq 0.36$, or possibly 0.5, or more generally $NA_o \leq NA_{det}$, a larger detector is desirable since due to Etendue considerations (as discussed above), since a larger M (generally requiring a larger detector for a given sample size) will allow a smaller $NA_i$ (image-side NA) for a given $NA_o$. Hence where light-collection requirements (e.g. to achieve a certain assay sensitivity) call for a large $NA_o$ (defined by $NA_o > NA_{det}$) and depth-of-focus and other design considerations (e.g. cost) allow for a large $NA_o$, a larger M is desirable such that losses are minimized at the detector. In such embodiments it can be useful to use a detector device, for example, one or more CCD devices, having a size of, or larger than, the area of the microfluidic device to be imaged. Use of such a large detector allows an increase in the magnification of the optical system, and hence (via etendue considerations) higher NA light collection from the sample for a fixed incident NA onto the detector (the latter set, e.g., by reflection losses at the CCD surface at high incoming ray incident angles).

A particularly preferred detector uses a CCD camera and an optical path that provides for a large field of view and a high numerical aperture to maximize the amount of light collected from each reaction chamber, thereby increasing detection sensitivity. In this regard, the CCD is used as an array of photodetectors wherein each pixel or group of pixels corresponds to a reaction chamber rather than being used to produce an image of the array. Thus, the optics may be altered such that image quality is reduced or defocused to increase the depth of field of the optical system to collect more light from each reaction chamber. In some embodiments, it is useful to employ high aspect ratio, or columnar chambers, to concentrate the sample to be interrogated by the detector along the optical axis of the optical system, and preferably by defocussing the image to increase the depth of field. Use of a low NA lens system, preferably a bilaterally symmetrical lens system is used. It is also useful to use a detector device, for example, one or more CCD devices, having a size of, or larger than, the area of the microfluidic device to be imaged. Used in conjunction with the low NA optics, improved detection sensitivity can be realized.

A detector system can include a light source for stimulating a reporter that generates a detectable signal. The type of light source utilized depends in part on the nature of the reporter being activated. Suitable light sources include, but are not limited to, lasers, laser diodes, white light sources, and high intensity lamps. If a laser is utilized, the laser can be utilized to scan across a set of detection sections or a single detection section. Laser diodes can be microfabricated into the microfluidic device itself. Alternatively, laser diodes can be fabricated into another device that is placed adjacent to the microfluidic device being utilized to conduct a thermal cycling reaction such that the laser light from the diode is directed into the detection section.

Detection can involve a number of non-optical approaches as well. For example, the detector can also include, for example, a temperature sensor, a conductivity sensor, a potentiometric sensor (e.g., pH electrode) and/or an amperometric sensor (e.g., to monitor oxidation and reduction reactions).

Certain intercalation dyes that that have dramatic fluorescent enhancement upon binding to double-stranded DNA, and/or show strong chemical affinity for double-stranded DNA, can be used to detect double-stranded amplified DNA. Examples of suitable dyes include, but are not limited to, SYBR™ and Pico Green (from Molecular Probes, Inc. of Eugene, Oreg.), ethidium bromide, propidium iodide, chromomycin, acridine orange, Hoechst 33258, Toto-1, Yoyo-1, and DAPI (4',6-diamidino-2-phenylindole hydrochloride). Additional discussion regarding the use of intercalation dyes is provided by Zhu et al., *Anal. Chem.* 66:1941-1948 (1994), which is incorporated by reference in its entirety.

As illustrated in FIG. 1A, some embodiments of the present invention provide a 1:1 imaging system adapted to generate and detect fluorescent, chemiluminescent, bioluminescent, and other signals from the microfluidic device. A 1:1 imaging system is provided in some embodiments that utilizes an image detection device as large as the sample to be imaged. By providing 1:1 imaging of a large field of view, on the order of several $cm^2$, embodiments of the present invention provide increased numerical aperture (NA) optical systems. Because light collection efficiency is approximately proportional to $NA^2$, the increase in NA provided by some embodiments of the present invention enable the collection of suitable fluorescent signals from reaction chambers comprising reaction volumes on the order of one to tens of nanoliters and active fluorophore concentrations on the order of 1.0 nanoMolar. In other embodiments, active fluorophore concentrations in picoMolar ranges provide suitable fluorescent signals.

Additionally, embodiments of the present invention provide for imaging systems that are slightly reducing, forming, for example, an image that ranges from about the same size as the object to about half the object size. For example, in an embodiment, an image of a spatial region of a microfluidic device is transmitted and captured, the spatial region being associated with more than 96 chambers. An image detecting device is used to capture the image of the spatial region using an image detection spatial region that is about equal to or slightly less in size than the spatial region of the microfluidic device. Merely by way of example, the ratio of the area of the spatial region of the microfluidic device to the area of the image of the spatial region can be 1:1, 1:0.99, 1:0.95, 1:0.9, 1:0.88, and 1:0.85. These particular ratios are merely exemplary, as the ratio selected for the imaging system will depend on the particular application.

In some embodiments, the optical imaging system includes a field of view of about 3 cm×3 cm. In other embodiments, the optical imaging system includes a field of view that ranges from about 1 cm×1 cm to about 5 cm×5 cm. In particular embodiments, an object field of view of 2 cm×2 cm, 2.5 cm×2.5 cm, 2.76 cm×2.76 cm, 3.07 cm×3.07 cm, 3.5 cm×3.5 cm, and 4 cm×4 cm, is provided. In general, the field of view of the optical imaging system is selected to correspond to the spatial region of the microfluidic device, for example, an area including a number of reaction chambers of interest.

Moreover, embodiments of the present invention provide optical imaging systems with a range of numerical apertures. As an example, an NA ranging from 0.1 to 0.5 is provided according to various embodiments. In a particular embodiment, NAs of 0.15, 0.18, 0.2, 0.23, 0.25, 0.3, 0.36, and 0.4 are provided.

The spatial resolution of the optical imaging system will generally be a function of the size of the pixels in the image detecting device. In some embodiments of the present invention, the magnification (equal to one for some embodiments) and the size of the pixels present in the detector will determine the number of pixels associated with each reaction chamber. Generally, it is preferable to have multiple detector pixels associated with each reaction chamber. For example, if a reaction chamber is 45 µm on a side, up to nine square pixels having a side dimension equal to 15 µm will overlap with the reaction chamber in the 1:1 imaging system. Thus, according to embodiments of the present invention, the number of pixels associated with each reaction chamber ranges from 1 to 100. For example, 4 pixel regions, 9 pixel regions, 16 pixel regions, 25 pixel regions, 36 pixel regions, 49 pixel regions, 64 pixel regions, and 81 pixel regions are associated with each reaction chamber according to some embodiments of the present invention.

In embodiments of the present invention, a range of pixel sizes from 1 $\mu m^2$ to 900 $\mu m^2$ are utilized. For example, square pixels 1 µm on a side, 2 µm on a side, 3 µm on a side, 4 µm on a side, 5 µm on a side, 10 µm on a side, 13.5 µm on a side, 15 µm on a side, 20 µm on a side, 25 µm on a side, and 30 µm on a side are utilized in various embodiments of the present invention. As will be evident to one of skill in the art, the pixel size, the detector array dimensions, and the number of pixels per array are related. In alternative embodiments, rectangular pixels with pixel areas ranging from 1 $\mu m^2$ to 900 $\mu m^2$ are utilized.

Moreover, detector arrays, also referred to as image detecting devices, including a range of pixel counts are utilized according to various embodiments of the present invention. Array dimensions range from 512×512 pixel regions to 3,000×3,000 pixel regions. Depending on the availability of detector arrays, greater numbers of pixels per array may be provided in some embodiments. In particular embodiments, array dimensions of 1,024×1,024 pixel regions and 2,048 by 2,048 pixel regions are utilized.

Embodiments of the present invention provide an optical imaging system characterized by several system parameters. For example, a working distance of greater than 35 mm, for instance, 45.92 mm is available through embodiments of the present invention. In another embodiment, a Root-Mean-Square (RMS) spot diameter averaging 13.44 µm with a maximum value of 17.85 µm is provided. Moreover, through embodiments of the present invention, an illumination variation of about ±5% is achieved. In some embodiments, the overall length of the optical imaging system is 542.1 mm with a maximum filter AOI of 12.56 degrees, a maximum beam diameter at the filter of 76 mm, a distortion of <0.10%, and a maximum lens diameter of 5.512 inches.

FIG. 1B is a simplified diagram for an imaging system according to an embodiment of the present invention. In some embodiments, the imaging system illustrated in FIG. 1B is utilized for imaging of microfluidic devices including devices adapted to perform protein crystallization processes. Additional details regarding imaging systems as illustrated in FIG. 1B and associated microfluidic devices are found in co-pending and commonly owned U.S. patent application Ser. No. 10/902,494, filed Jul. 28, 2004 and U.S. patent application Ser. No. 10/851,777, filed May 20, 2004, the disclosures of which are incorporated by reference herein for all purposes. In particular, additional details regarding microfluidic devices provided according to embodiments of the present invention and their use in conjunction with the imaging system as shown in FIG. 1B are found therein. These diagrams are merely examples, which should not unduly limit the scope of the claims herein. One of ordinary skill in the art would recognize many variations, alternatives, and modifications.

Imaging system (10) operates, in one embodiment, in the following manner. First, microfluidic device (30) is securely placed on stage (20). Based on a fixed feature of the microfluidic device (30), for example, an edge of the base support of microfluidic device (30), computer (110) then causes x,y drive (25) to move stage (20) about to align microfluidic device (30) in a first x,y position with a first of a plurality of fiducial markings, wherein the fiducial markings are embedded within the microfluidic device at a known z dimension distance from a chamber center point, comes into focus by imaging device (60) based on dead reckoning from the fixed feature. A user of the system then registers the precise coordinate of the fiducial with the imaging system. Two or more additional fiducial marks are then likewise mapped with the assistance of a user. In other embodiments, this process is automatic as the centroids of the fiducials can be calculated precisely by locating the symmetric XY fiducial object and removing any non-symmetric components. Imaging device (60), under the control of computer (110) then adjusts the z dimension location of focal plane (100) to focus upon the fiducial marking. For example, once focused upon the first fiducial marking, the imaging system then obtains a first x,y coordinate image of microfluidic device (30) looking for additional fiducial markings within the field of view of imaging device (60). In preferred embodiments, the field of view can embrace an entire metering cell. The computer then analyzes the first x,y coordinate image to determine whether the microfluidic device has skew and stretch, and if skew or stretch are determined, transforms the first x,y image to align the image and coordinate map of the microfluidic device to an idealized coordinate map. The idealized coordinate map is used later during image subtraction and masking steps.

In preferred embodiments, with the microfluidic device x,y coordinate image aligned against the ideal coordinate map, the system then determines whether the stretch, distortion or lack of co-registration between the various microfluidic layers is present in the microfluidic device by comparing the location of the fiducial markings in the x,y coordinate image with the fiducial markings locations in the x,y coordinate image of the ideal stored image map. If differences are present between the actual fiducial locations and the imaged fiducial locations, a matrix transformation, preferably an Affine transformation, is performed to transform the imaged shape of the metering cell into a virtual shape of the ideal metering cell shape. By converting the actual image to a known and fixed ideal image using the matrix transformation computed from the differences between the measured actual fiducial locations and the stored ideal fiducial locations, image subtraction and other image analysis are made possible.

By computing the differences between the coordinate maps through matrix analysis, a matrix transformation may be developed to reform the actual image into an ideal image for use in further image processing described herein. By causing the imaged microfluidic device to conform to a standard shape, image subtraction and masking is possible to maximize the viewable area of a metering cell chamber. Moreover, if defects or debris are present within the chamber at time zero in a series of time based images, such defects or debris can be masked out of subsequent images to avoid false signals when applying automated analysis. In addition to masking off areas of the chambers which contain defects or debris, the walls of the chambers may be subtracted from subsequent images, again so as to not cause false readings in the subsequent analysis. The discrepancy between various layers, such as between the control layer and the channel layer, can also be calculated based on the position of a found object in the control layer, such as the control lines themselves. In another example, this correction is determined based on the control layer fiducials themselves. For certain embodiments, this extra transformation is important since the control layer partitions the protein chamber from the rest of the control line.

Figure 10:
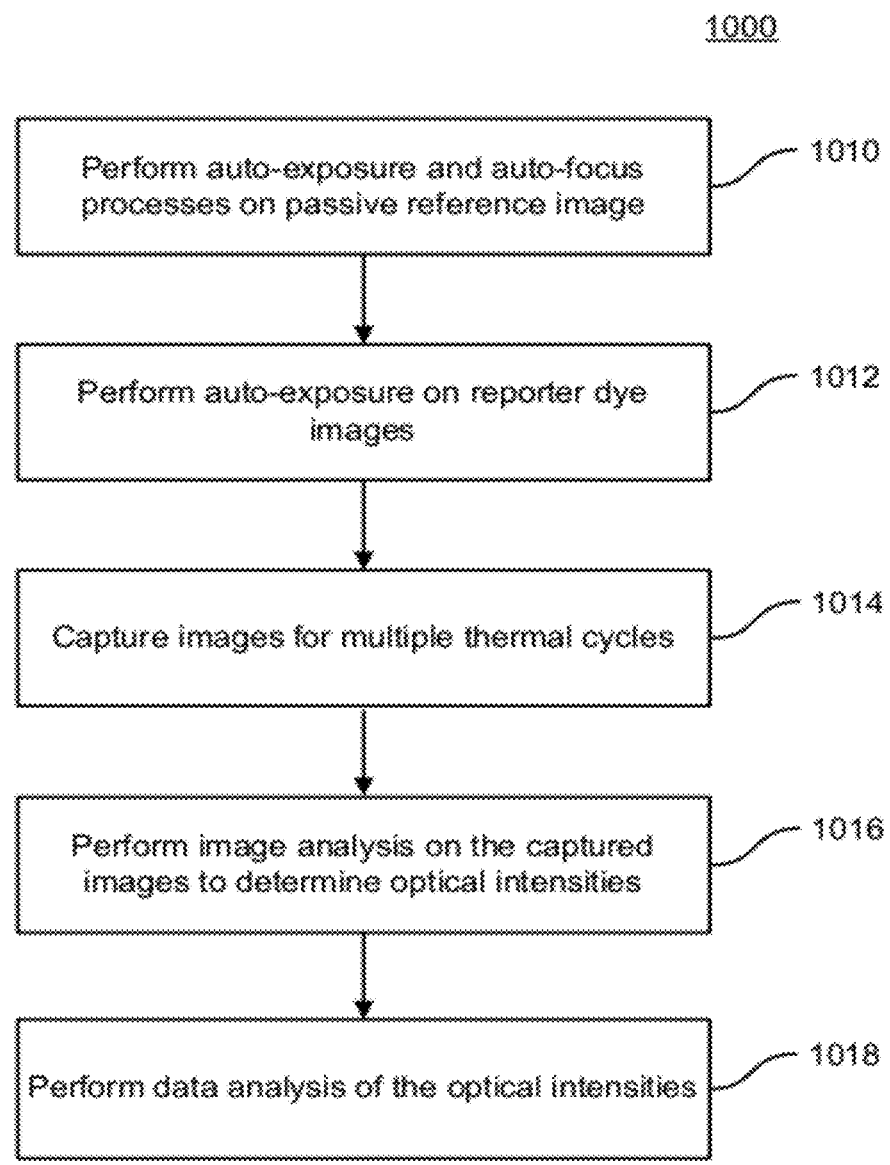
FIG. 10 is a simplified flowchart illustrating a method for performing image processing according to an embodiment of the present invention.

FIG. 10 is a simplified flowchart illustrating a method for performing image processing according to an embodiment of the present invention. The method 1000 includes performing auto-exposure and auto-focus processes on a passive reference image (1010). As described more fully throughout the present specification, various methods for performing auto-exposure and auto-focus are provided herein. For example, auto-exposure methods and techniques are described with reference to FIGS. 4A-4C and auto-focus methods and techniques are described with reference to FIGS. 2 and 3. Auto-exposure processes are performed using reporter dye images (1012). In various embodiments, one or both reporter dyes are utilized in the image acquisition and analysis processes.

Images are captured for multiple thermal cycles (1014). As an example, 40 PCR thermal cycles are performed in some applications and images are captured for three dyes (one passive reference and two reporters). Thus, 120 images are captured during the 40 thermal cycles. In this image capture process, the computed auto-exposure and auto-focus parameters determined in steps 1010 and 1012 are utilized. Image analysis is performed (1016) on the sequence of images to extract optical signal intensities in the PCR reaction chambers as a function of cycle number. In an embodiment utilizing a 48×48 microfluidic device, each of the 2,304 chambers are analyzed for each image associated with the series of 40 cycles for each of the dyes. Additional discussion of a method of extracting optical signal data from chambers in the images as a function of the PCR cycles is provided with reference to FIG. 11 below.

Data analysis is performed (1018) of the optical intensities extracted in step 1016. For gene expression applications, the 40 point DNA amplification curve is analyzed to determine the change in threshold (Ct) value associated with each reaction chamber. Accordingly, for a 48×48 microfluidic device, 2,304 Ct values are provided by the method illustrated in FIG. 10.

Figure 5A:
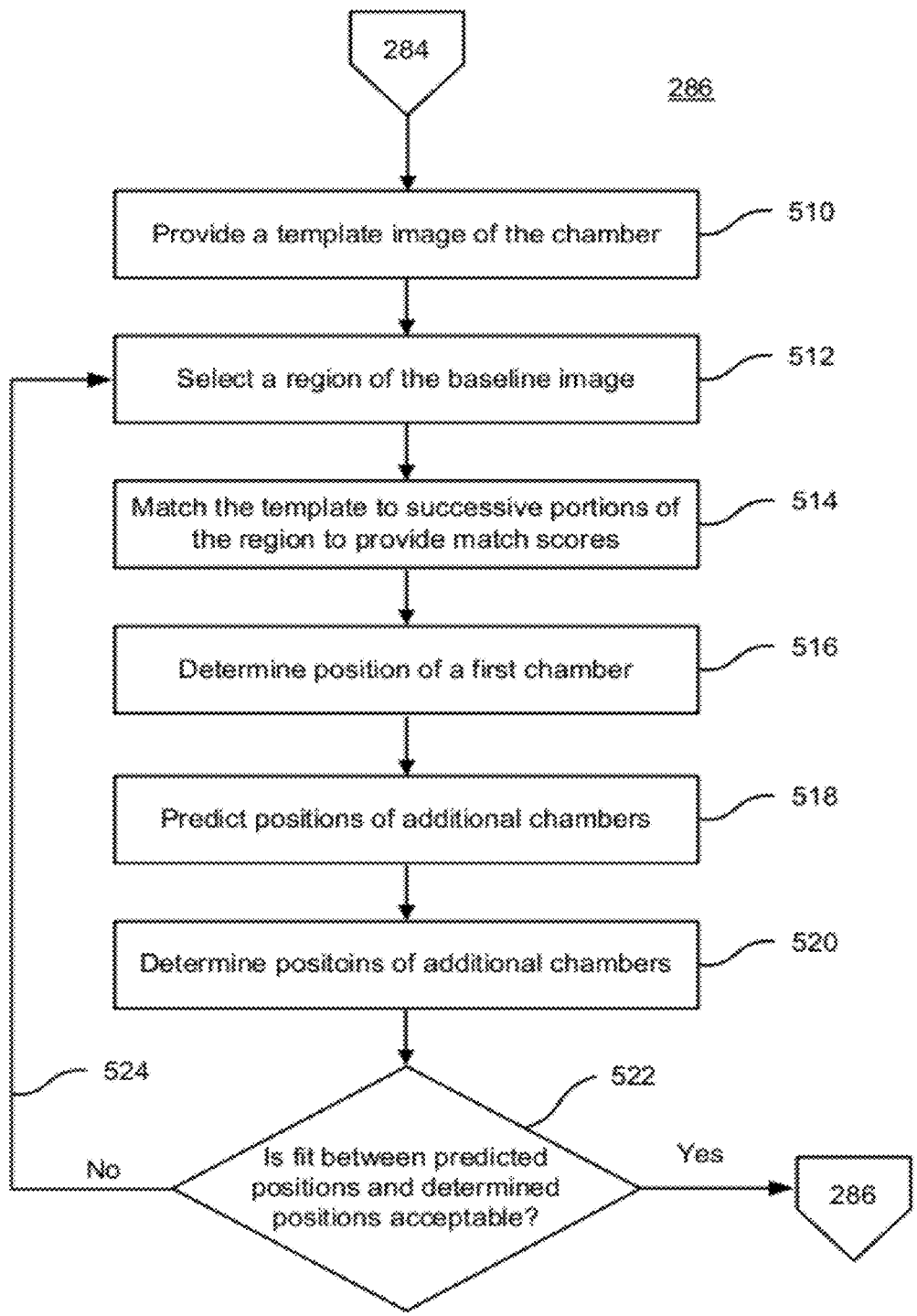
FIG. 5A is a simplified flowchart illustrating a method of determining chamber positions according to an embodiment of the present invention.
Figure 5B:
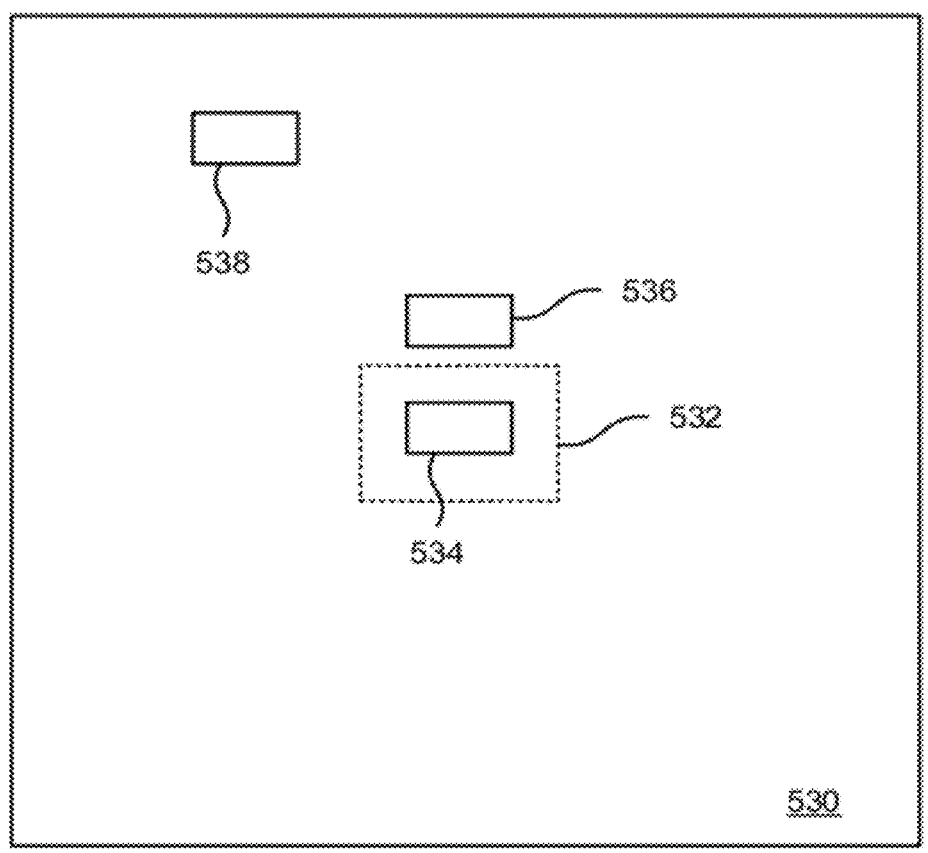
FIG. 5B is a simplified schematic illustration of a microfluidic device according to an embodiment of the present invention.
Figure 11:
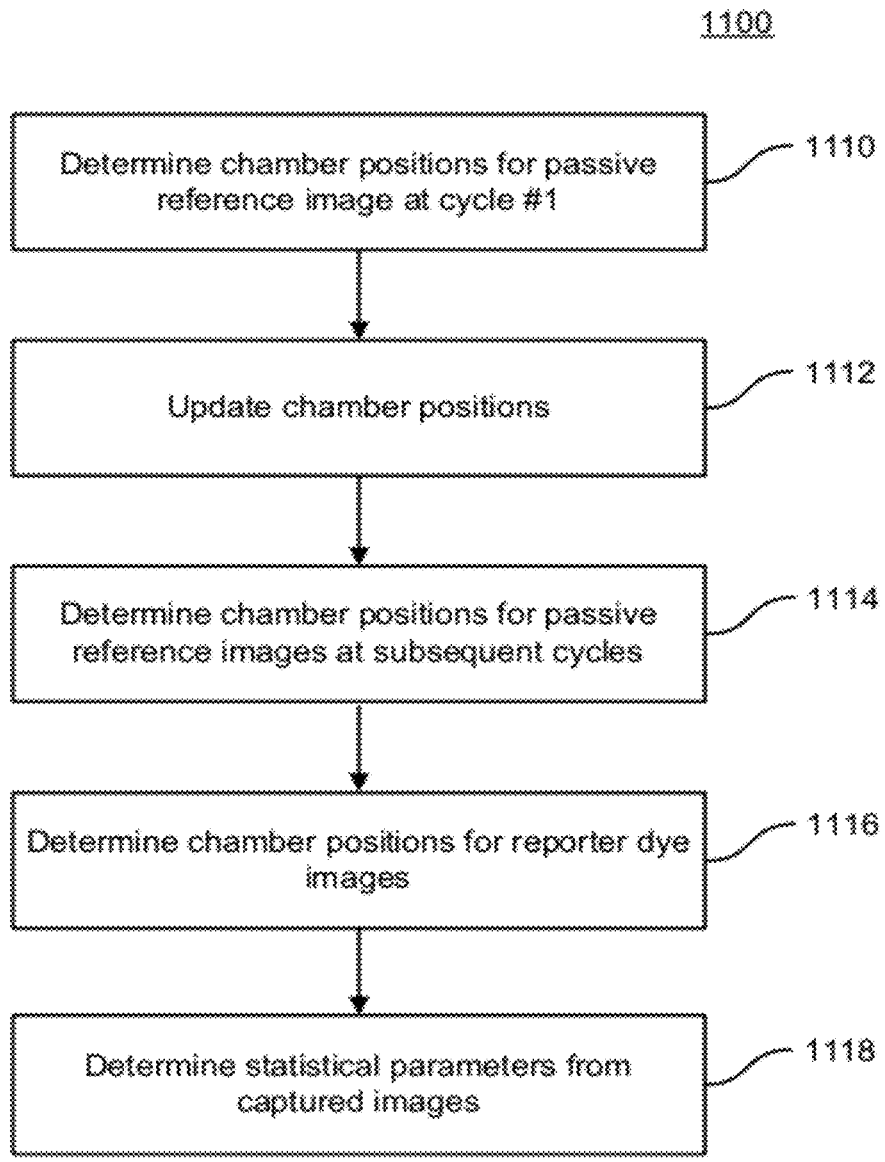
FIG. 11 is a simplified flowchart illustrating a method of extracting optical signal data from PCR reaction chambers according to an embodiment of the present invention.

FIG. 11 is a simplified flowchart illustrating a method of extracting optical signal data from PCR reaction chambers according to an embodiment of the present invention. According to method 1100, chamber positions are determined (1110) for the passive reference image for the first PCR cycle. In an embodiment, the methods and techniques described with reference to FIGS. 5A and 5B are utilized to determine chamber positions. Chamber positions are then updated (1112). In step 1112, fine tuning of the chamber positions is performed for each individual chamber. Accordingly, after step 1112, the edges of the chamber coincide with a strong response from an edge detection operator.

Chamber positions are then determined (1114) for passive reference images at subsequent cycles (e.g., 2, 3, 4, . . . 40). The chamber positions determined in step 1110 and 1112 are utilized as initial estimates of the chamber positions for this process. After initial chamber positions are determined, fine tuning may be performed as appropriate to the particular applications. After the completion of step 1114, chamber positions for the passive reference images at all thermal cycles are available for subsequent processing.

Chamber positions are determined (1116) for reporter dye images for all PCR cycles. The chamber positions determined for the passive reference images are utilized as initial estimates in determining these chamber positions. In an embodiment, 40 images are utilized for each reporter dye. After initial chamber positions are determined, fine tuning may be performed as appropriate to the particular applications.

One or more statistical parameters are extracted from the intensity data associated with the chambers in the captured images (1118). In an embodiment, an average value of the intensity for each chamber is determined by considering pixel chambers as well as a number of pixels from an area adjacent the particular chamber. As an example, the area analyzed in slightly larger (e.g., by including a one pixel wide boundary around the perimeter of the chamber) than the chamber dimensions so that noise in the extracted intensity value as a result of shift errors in chamber locations is reduced.

Figure 2:
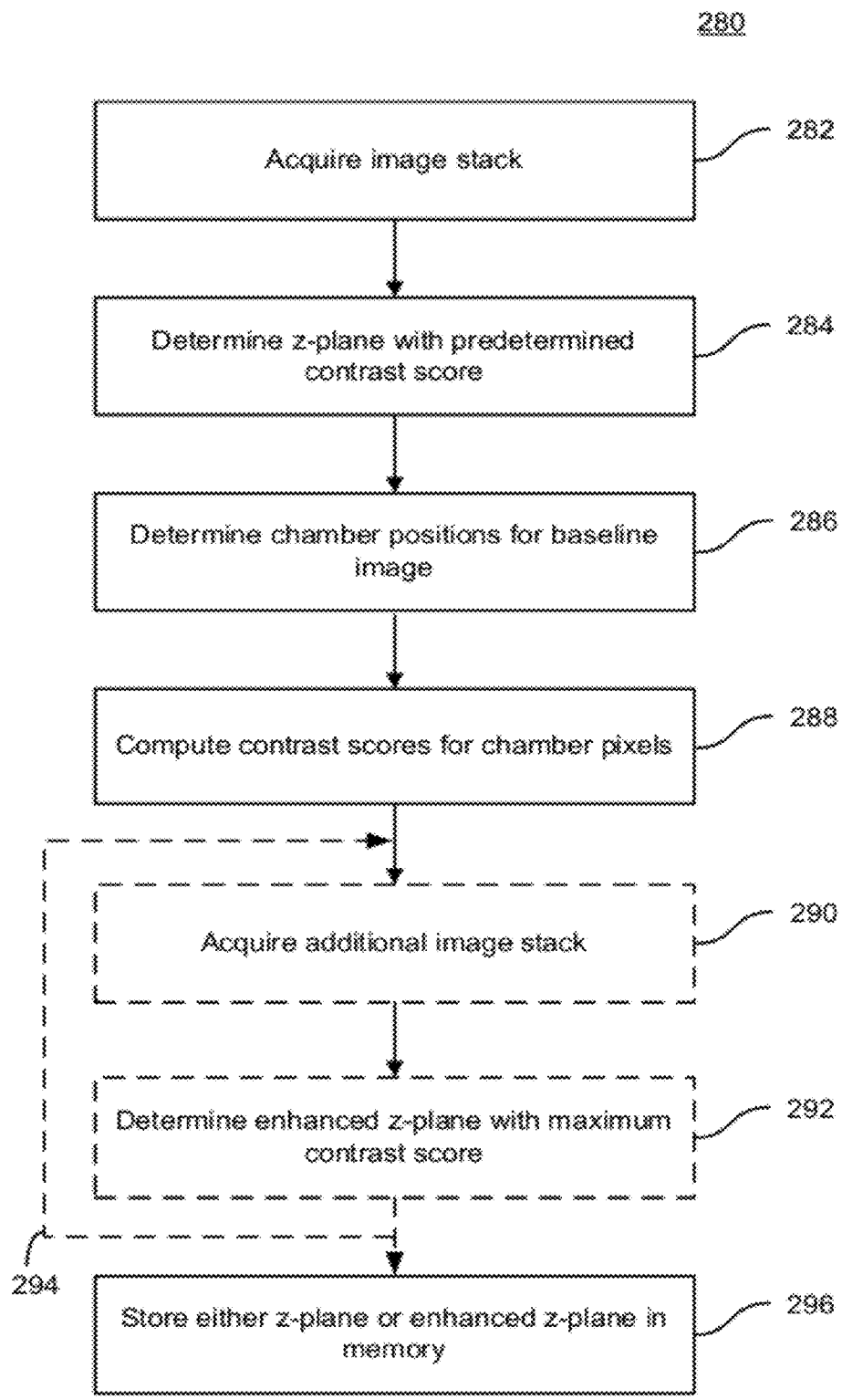
FIG. 2 is a simplified flowchart illustrating a method of determining a focal plane for imaging a microfluidic device according to an embodiment of the present invention.

FIG. 2 is a simplified flowchart illustrating a method of determining a focal plane for imaging a microfluidic device according to an embodiment of the present invention. According to some embodiments, the method illustrated in FIG. 2 is referred to as an auto-focus algorithm. As described more fully below, embodiments of the present invention provide methods and systems for auto-focusing of image acquisition processes. Thus, image quality and detection sensitivity are increased in comparison with conventional methods. Method 280 includes acquiring a stack of images at a series of predetermined focal distances (282). According to embodiments of the present invention, the stack of images are acquired at a series of z-positions, also referred to as focal distances. In an embodiment, 100 images are acquired at a spacing of 100 μm between z-positions. Of course, alternative embodiments acquire a larger or smaller number of images at larger or smaller spacings. One of ordinary skill in the art would recognize many variations, modifications, and alternatives.

The method also includes determining a z-plane with a predetermined contrast score (284). An edge detection operator is used to analyze the images from the stack of images and to determine contrast scores associated with each image. Chambers provided on microfluidic devices analyzed using embodiments of the present invention typically have a chamber thickness on the order of 300 μm. Thus, many of the images in the stack of images will be focused on planes other than a plane containing reaction chambers. For some images in the stack of images, control lines and other features present on the microfluidic device will provide a certain contrast score. Preferably, the highest contrast scores will be associated with the planes including cross-sections of the reaction chambers. In a specific embodiment, several of the images will include cross-sections of the reaction chambers and will be characterized by contrast scores higher than a threshold value. Generally, the threshold value is selected to be greater than a contrast value associated with background features, for example, control lines.

In a particular embodiment, the image that is characterized by the maximum contrast score is selected and referred to as a baseline image. Of course, it is not required that the baseline image be the image with the maximum contrast score selected from all the images in the stack. It will be appreciated that other images will also be suitable for additional processing as described below. In some embodiments, a sample of the images in the image stack are utilized for processing by the edge detection operator. Thus, sampling of the images increases stack scanning speed, with additional processing then performed on images in the vicinity of images with higher contrast scores. One of ordinary skill in the art would recognize many variations, modifications, and alternatives.

Although step 284 has been described with respect to an edge detection operator, this particular operator is not required by embodiments of the present invention. Other image processing operators that provide space-frequency analysis are also included within the scope of embodiments of the present invention. Merely by way of example, wavelet operators may also be utilized.

The chamber positions are determined (286) using an algorithm that performs image processing of the baseline image. For example, an algorithm that considers individual pixels or groups of pixels at a predetermined position on the image is used in an embodiment to determine the chamber positions. Generally, data related to the design of the microfluidic device, which has been previously stored in one or more memories, is utilized during the chamber position determination process. The chambers or sample wells may contain reagents and samples during the chamber position determining process or may be empty. According to embodiments of the present invention, the chambers are also referred to as sample wells and reaction chambers. Such references are not intended to limit the scope of embodiments as described throughout the present specification.

FIG. 5A is a simplified flowchart illustrating a method of determining chamber positions according to an embodiment of the present invention. In FIG. 5A, steps 510-522 represent the process represented by step 286 in FIG. 2. A template image of the chamber is built or provided (510). Referring to FIG. 5B, which is a simplified schematic illustration of a microfluidic device, the template is represented by reference number 538. A region 532 of the baseline image is selected (512) for image processing. As illustrated in FIG. 5B, the region 532 is located at a portion of the microfluidic device 530 in which at least one chamber is expected to be found. The template 538 is matched to successive portions of the region 532 to provide a number of match scores (514). From this number of match scores, one or more locations characterized by match scores greater than a predetermined match score are determined. In a particular embodiment, the template is matched against all the locations inside region 532. Typically, of the one or more locations characterized by match scores greater than the predetermined value, one of the locations will have a maximum match score. Thus, in some embodiments, the location with the maximum match score is utilized to determine the position of the first chamber (516). Referring to FIG. 5B, the first chamber is illustrated by reference number 534. The terms position and location are utilized interchangeably herein and are not intended to limit the scope of embodiments of the present invention.

In a particular embodiment, several locations with match scores greater than the predetermined match score may be utilized, for example, using an averaging or weighting technique to determine the position of the first chamber. As illustrated in FIG. 5B, the region 532 and the first chamber 534 are located at a generally central portion of the microfluidic device 530, but this is not required by embodiments of the present invention. In alternative embodiments, the region 532 and the first chamber 534 are located at other positions, including peripheral positions. One of ordinary skill in the art would recognize many variations, modifications, and alternatives.

The locations of additional chambers are predicted (518) and located (520). In an embodiment, prediction of additional chamber location is performed by moving radially outwards from the location of the first chamber. The prediction is based, in an embodiment, on design information previously provided. Finding the locations of additional chambers is performed by using the template matching process described with reference to step 514. Appropriate regions are selected for use in the template matching process. In a specific embodiment, a linear model of the grid pattern present in the microfluidic device is generated and refined as the number of additional chambers located increases. Refined versions of the linear model may be used as part of the prediction model, thereby increasing the accuracy of the prediction model as more additional chambers are located.

If the fit between the predicted locations and the determined locations for a certain number of chambers is less than a predetermined value, then portions of process 286 are repeated as illustrated by branch 524 in FIG. 5A. During the process of repeating steps 512-522, the location of the region is adjusted to begin the initial search for the first chamber at a different location on the microfluidic device. The process may also be repeated if the match scores obtained are less than a predetermined value. On the other hand, if the fit between the predicted locations and the determined locations is acceptable, then the process proceeds to step 286. Generally, the number of times the process is repeated is limited to an appropriate value and user intervention or a manual process is utilized to prevent endless loops being introduced into the chamber finding algorithms.

In a particular embodiment, the intensity distribution of the pixels in the baseline image is analyzed to determine the position of a first chamber. Then, the determination of a first chamber position is utilized in some applications, along with design data, to predict chamber position for subsequently determined chambers. One of ordinary skill in the art would recognize many variations, modifications, and alternatives.

The process of determining the chamber positions is not limited to the use of the baseline image. Utilizing embodiments of the present invention, multiple images, including, but not limited to the baseline image, are candidates for use with the chamber positioning algorithms.

Because the images in the stack of images are registered with some precision in the x-y plane, once the chamber positions have been determined for the baseline image, the same chamber position locations may be applied to the other images in the stack. It is possible to perform other chamber positioning processes, including processing of images other than the baseline image, as appropriate to a particular application.

The contrast scores are recomputed for the images in the stack, now considering the chamber pixels (288). In an embodiment, only the chamber pixels are utilized in recomputing the contrast scores. Generally, the edge detection operator utilized in step 284 is used to recompute the contrast scores. The use of the chamber pixels enables the computation process to effectively remove the portion of the contrast score resulting from features such as control lines and the like. Accordingly, the contrast score recomputed in step 288 is largely determined by the presence of chamber features. The image acquired in the image plane characterized by the maximum recomputed contrast score is labeled as the updated baseline image.

Figure 6A:
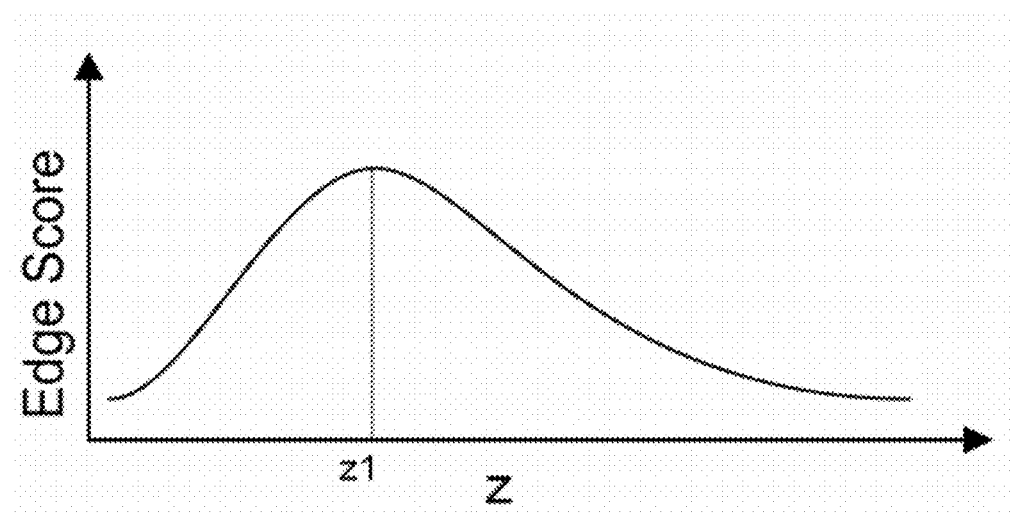
FIGS. 6A and 6B are simplified contrast score plots for different z-planes according to an embodiment of the present invention.
Figure 6B:
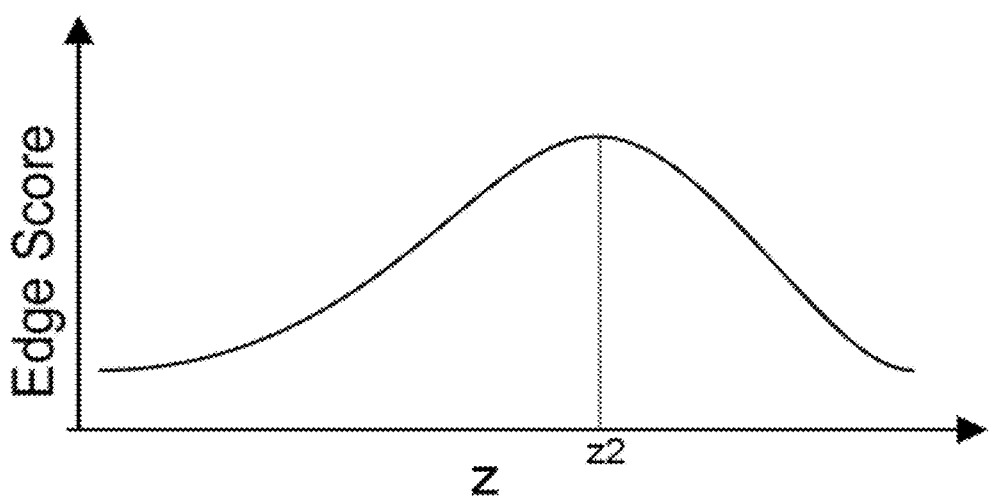

FIGS. 6A and 6B are simplified contrast score plots for different z-planes according to an embodiment of the present invention. The contrast score plot illustrated in FIG. 6A corresponds to an embodiment of step 284 and the contrast score plot illustrated in FIG. 6B corresponds to an embodiment of step 288. Referring to FIG. 6A, an edge detection operator is utilized to generate a contrast score (i.e., edge score) as a function of position. As illustrated in FIG. 6A, the z-plane ($z_1$) associated with the maximum edge score is determined. The chamber finding routine illustrated in FIG. 5A is then utilized to determine the positions of the various chambers. Utilizing these chamber positions, FIG. 6B illustrates the edge scores obtained by considering only pixels located in the chambers. As a result of the removal of pixels associated with background features, the z-plane ($z_2$) associated with the maximum contrast score is shifted in position to a different z-plane.

Generally, the z-position of the updated baseline image will be in the vicinity of the baseline image. In a specific embodiment, the updated baseline image will be the same as the baseline image, although this result is not required by embodiments of the present invention. The reduction of background noise provided by the use of chamber pixels typically provides the selection of an updated baseline image more closely aligned with the reaction chambers.

An additional image stack is optionally acquired (290) at a series of planes at z-positions on either side of the updated baseline image. The spacing between the images in the additional image stack is typically less than the spacing between the images acquired in step 282. In an embodiment, 16 images are acquired at a spacing of 20 µm between z-positions. Of course, alternative embodiments acquire a larger or smaller number of images at larger or smaller spacings. One of ordinary skill in the art would recognize many variations, modifications, and alternatives.

The images in the additional image stack are optionally analyzed (292) to compute the contrast scores for these images. In an embodiment, only chamber pixels are utilized during this analysis to reduce the impact of background features on the computed contrast scores. The process of acquisition and computations in optional steps 290 and 292 provides an enhanced resolution updated baseline image located at an enhanced z-plane. The processes performed in steps 290 and 292 may be repeated a number of times (294) depending on the desired z-position resolution for the final baseline image. In a particular embodiment, steps 290 and 292 are performed once, improving the resolution associated with the enhanced resolution updated baseline image.

The z-plane associated with the updated baseline image determined in step 284 or the enhanced z-plane associated with the enhanced resolution updated baseline image (if optional steps 290 and 292 are utilized) is stored in a memory (296). This stored position, associated with the z-position of the reaction chambers is utilized in subsequent processes as described more fully throughout the present specification.

Figure 3:
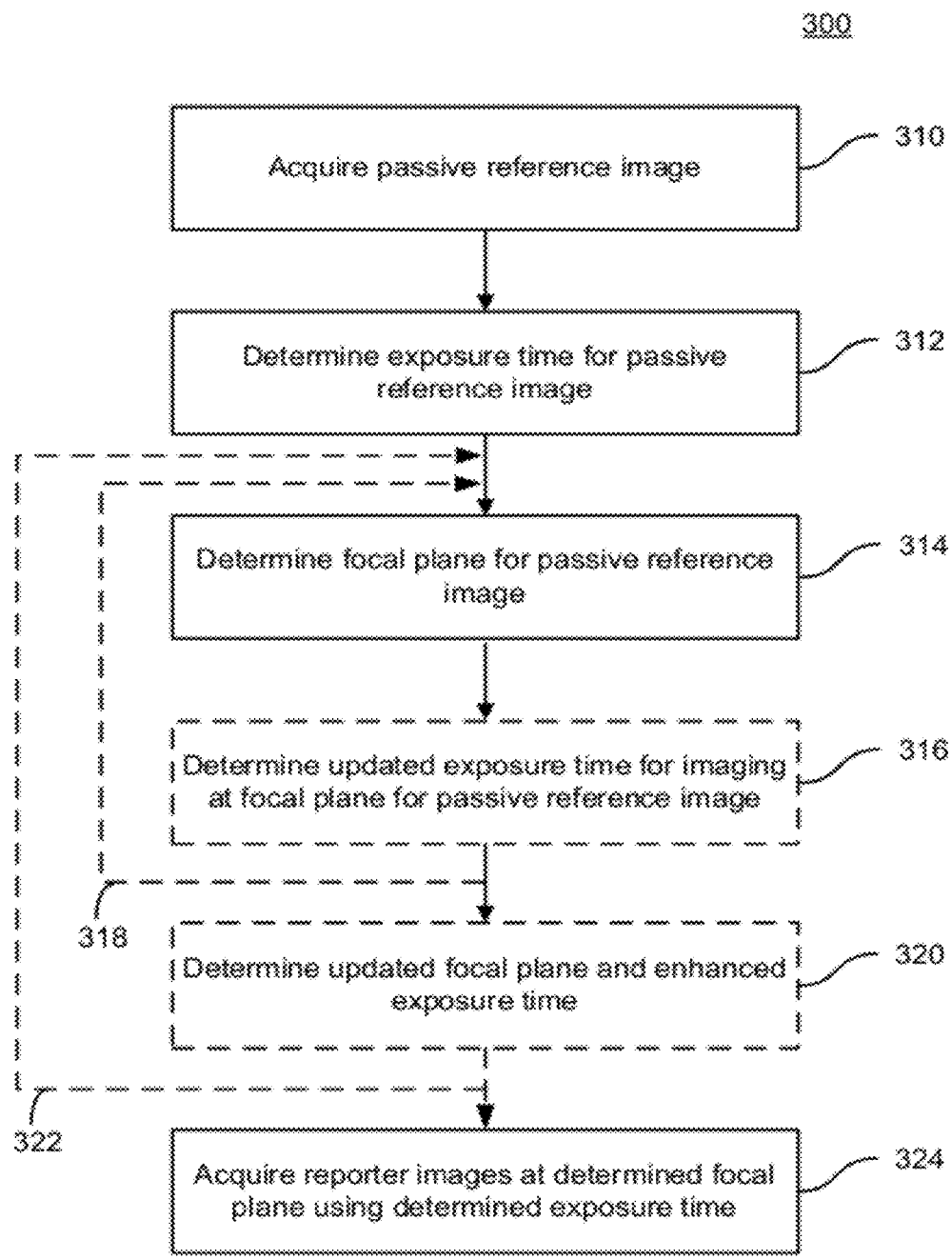
FIG. 3 is a simplified flowchart illustrating a method of acquiring reporter images utilizing a microfluidic device according to an embodiment of the present invention.

FIG. 3 is a simplified flowchart illustrating a method of acquiring reporter images utilizing a microfluidic device according to an embodiment of the present invention. Method 300 includes acquiring a passive reference image (310). The sample utilized in the microfluidic devices described herein includes a passive reference dye, for example, ROX, utilized to provide information related to the amount of sample in the reaction chamber. The reagent utilized in the microfluidic devices described herein includes one or more reporter dyes, for example, FAM or VIC, utilized to provide information related to the reactions occurring in the reaction chamber. Of course, the use of other dyes is included within the scope of embodiments of the present invention.

Figure 4A:
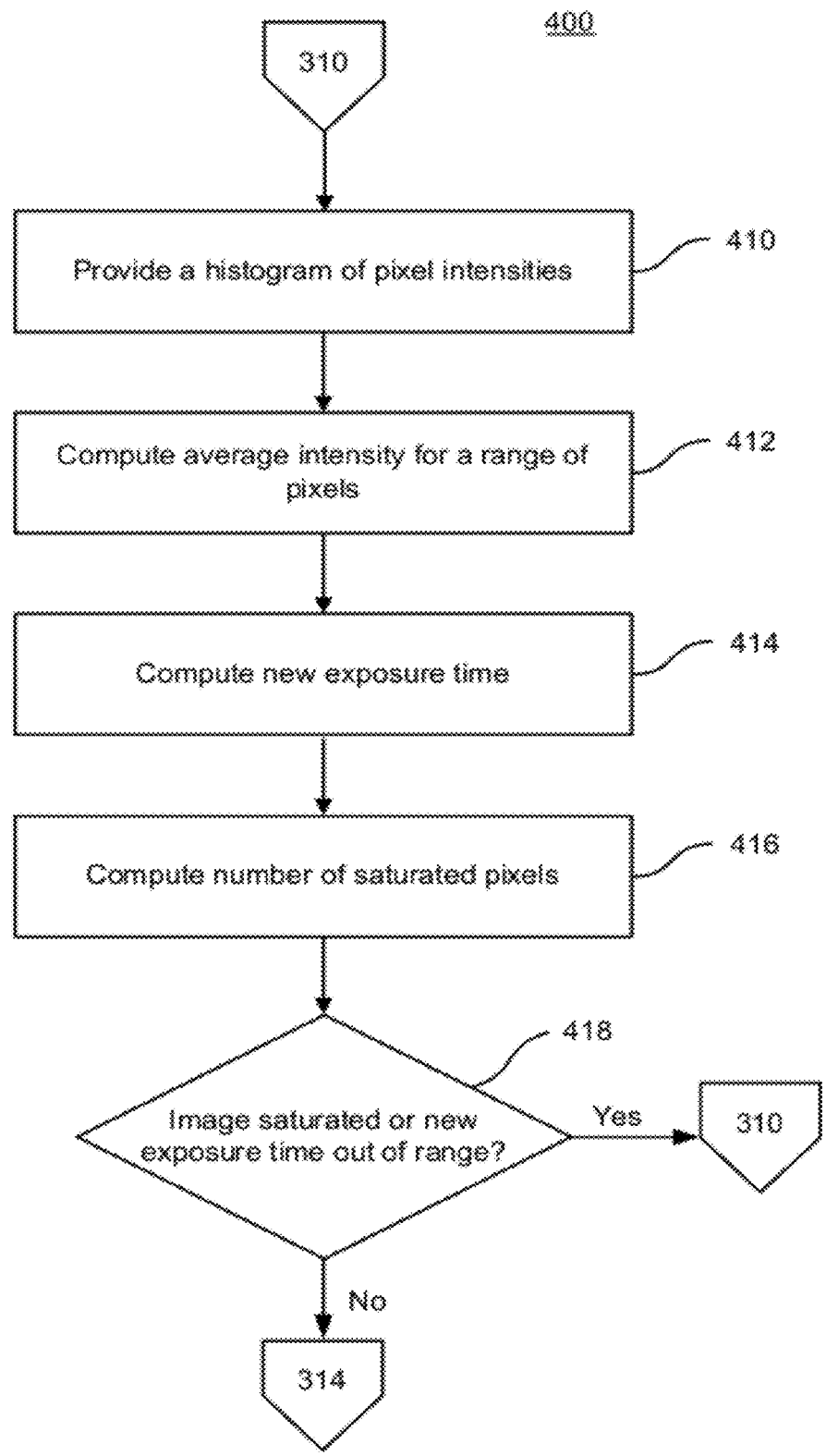
FIG. 4A is a simplified flowchart illustrating a method of determining an exposure time for acquisition of a passive reference image according to an embodiment of the present invention.

The passive reference image is analyzed to determine an exposure time for acquisition of a passive reference image (312). FIG. 4A is a simplified flowchart illustrating a method of determining an exposure time for acquisition of a passive reference image according to an embodiment of the present invention. Utilizing embodiments of the present invention, methods and systems are provided in which auto-exposure routines result in emission from the passive reference and the reporter dyes within a desired range. Exposure times are provided such that emission from the reporter dye, which increases as a function of time as a result of additional DNA created during amplification in some reactions, is not saturated after a predetermined number of amplification cycles. Accordingly, dynamic adjustment of exposure time is provided herein as exposure times are modified as a function of the measured signal. For example, these dynamic exposure techniques account for increases in fluorescence resulting from reactions or variations in dye intensity. Thus, embodiments of the present invention reduce adverse effects resulting from saturation, which can result in electrons bleaching into adjacent pixels, thereby corrupting data from adjacent chambers.

Referring to FIG. 4A, the method of determining an exposure time for the passive reference image includes providing or building a histogram of pixel intensities (410). In an embodiment, only pixels associated with chambers (chamber pixels) are considered in building the histogram of pixel intensities. In this embodiment, the histogram is therefore largely dependent on features in the chambers and not background features. Typically, the histogram is a single-peak distribution centered at a given intensity value. The average intensity ($J_0$) is computed for a range of pixels (412). The range of pixels is a predetermined range spanning from a first percentile to a second percentile. As an example, the average intensity may be computed for a range of 20 percentile points, i.e., pixels with intensity between the 75th percentile and the 95th percentile. In other embodiments, the range is varied as appropriate to the particular applications.

A new exposure time ($t_1$) is computed (414) utilizing the formula in equation (1):

$$t_1 = \frac{J_1}{J_0} \cdot t_0, \quad (1)$$

where $J_1$ is the target intensity. The target intensity is a predetermined value dependent, in part, on the type of dye utilized. The computation in equation (1) includes the assumption that intensity is linearly proportional to exposure time, an assumption that is valid for many applications provided according to embodiments of the present invention. The new exposure time is compared to a set of predetermined threshold values to determine if the new exposure time is outside of a desired range. In an embodiment, the minimum predetermined threshold values is 100 ms and the maximum predetermined threshold value is 2,000 ms. If the new exposure time is outside the range defined by the set of predetermined threshold values, then the new exposure time is determined to be out of range.

The number of saturated pixels is computed (416) and compared to a predetermined threshold. If the number of saturated pixels exceeds the predetermined threshold, then the image acquired in step 310 is considered to be saturated. Merely by way of example, the predetermined threshold is 2% according to an embodiment of the present invention. In other embodiments, the predetermined threshold is larger or smaller depending on the particular application. If the image is saturated or if the new exposure time is out of range (418), then the process returns to step 310, in which a new passive reference image is acquired. It should be noted that when the process returns to step 310, the new exposure time (rather than the original default exposure time) is utilized during the image acquisition process. If the image is not saturated and the new exposure time is in the range defined by the set of predetermined threshold values, then the process continues to step 314 as illustrated in FIG. 3. In an embodiment, if the results provided by process 400 are not acceptable to the user after a predetermined number of cycles, a manual exposure mode is utilized.

Figure 4B:
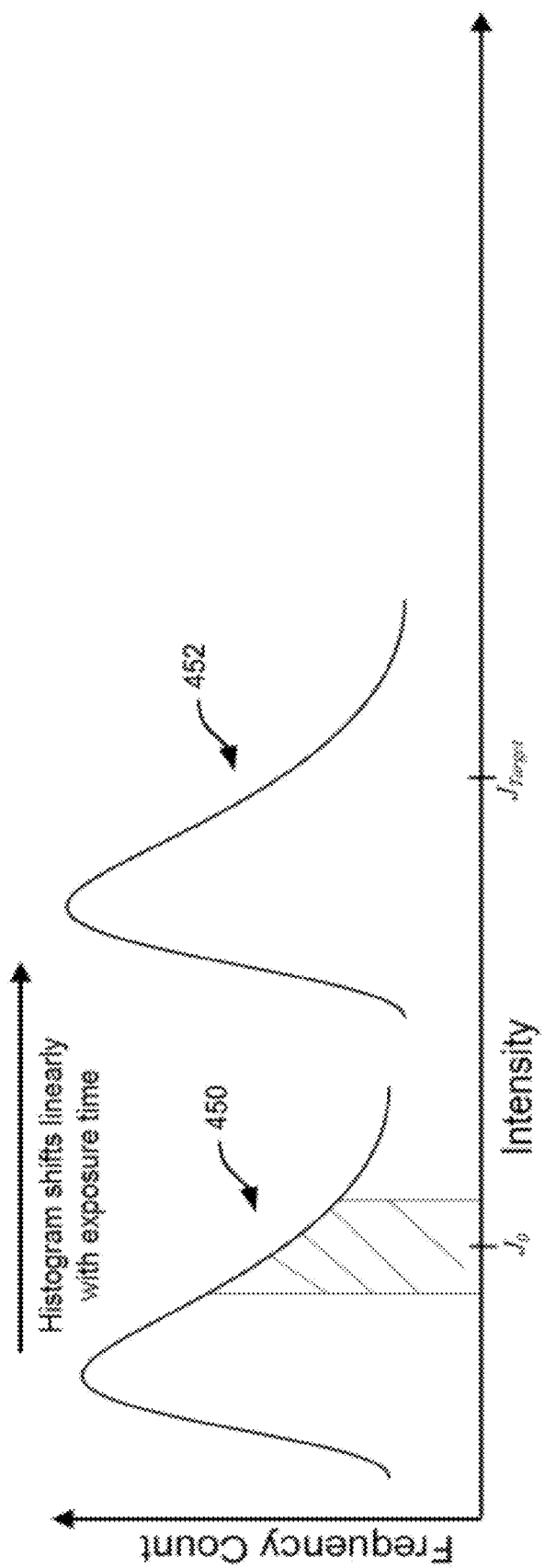
FIG. 4B is simplified diagram illustrating a histogram of pixel intensities as a function of intensity according to an embodiment of the present invention.

FIG. 4B is simplified diagram illustrating a histogram of pixel intensities as a function of intensity according to an embodiment of the present invention. Two time periods are illustrated in FIG. 4B, with the histogram for a first exposure time illustrated by reference number 450 and the histogram for a second (and later) exposure time illustrated by reference number 452. The average intensity ($J_0$) for the range of pixels illustrated by the shaded region is illustrated. As the exposure time is increased, the histogram shifts to the right, approaching the target intensity ($J_{Target}$). As described above, an iterative process is utilized in some embodiments to determine an exposure time appropriate to the particular applications.

Figure 4C:
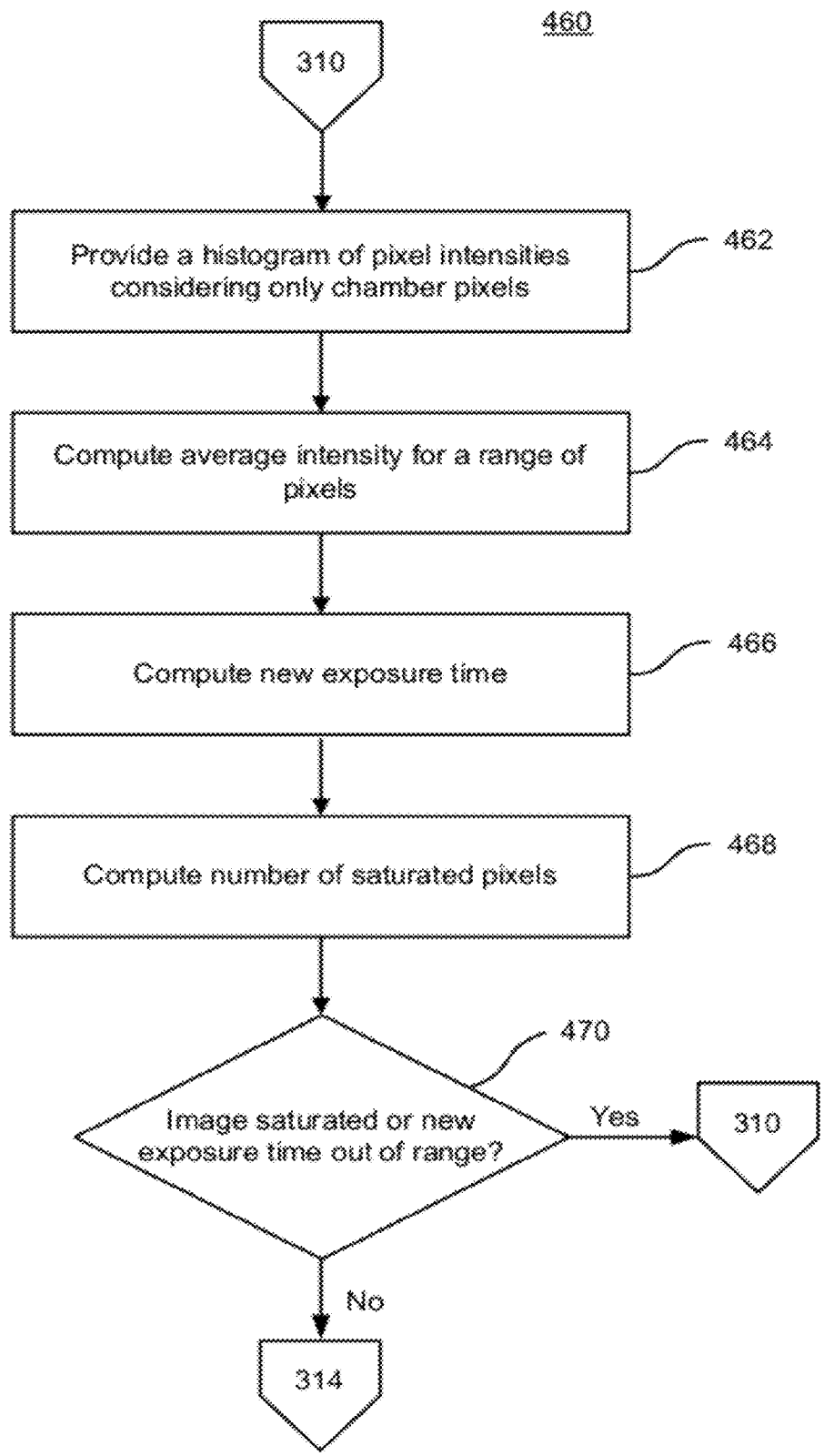
FIG. 4C is a simplified flowchart illustrating a method of determining an exposure time for acquisition of a passive reference image according to another embodiment of the present invention.

FIG. 4C is a simplified flowchart illustrating a method of determining an exposure time for acquisition of a passive reference image according to another embodiment of the present invention. A histogram of pixel intensities is provided or built using only chamber pixels (462). As a result of using chamber pixels, the histogram is largely dependent on features in the chambers and not background features. Typically, the histogram is a single-peak distribution centered at a given intensity value. The average intensity ($J_0$) is computed for a range of pixels (464). The range of pixels is a predetermined range spanning from a first percentile to a second percentile. As an example, the average intensity may be computed for a range of 20 percentile points, i.e., pixels with intensity between the 75th percentile and the 95th percentile. In other embodiments, the range is varied as appropriate to the particular applications.

A new exposure time ($t_1$) is computed (466) utilizing the formula in equation (2):

$$t_1 = \frac{J_1}{J_0} \cdot t_0, \quad (2)$$

where $J_1$ is the target intensity. The target intensity is a predetermined value dependent, in part, on the type of dye utilized. The computation in equation (2) includes the assumption that intensity is linearly proportional to exposure time, an assumption that is valid for many applications provided according to embodiments of the present invention. The new exposure time is compared to a set of predetermined threshold values to determine if the new exposure time is outside of a desired range. In an embodiment, the minimum predetermined threshold values is 100 ms and the maximum predetermined threshold value is 2,000 ms. If the new exposure time is outside the range defined by the set of predetermined threshold values, then the new exposure time is determined to be out of range.

The number of saturated pixels is computed (468) and compared to a predetermined threshold. If the number of saturated pixels exceeds the predetermined threshold, then the image acquired in step 310 is considered to be saturated. Merely by way of example, the predetermined threshold is 2% according to an embodiment of the present invention. In other embodiments, the predetermined threshold is larger or smaller depending on the particular application. If the image is saturated or if the new exposure time is out of range (470), then the process returns to step 310, in which a new passive reference image is acquired. It should be noted that when the process returns to step 310, the new exposure time (rather than the original default exposure time) is utilized during the image acquisition process. If the image is not saturated and the new exposure time is in the range defined by the set of predetermined threshold values, then the process continues to step 314 as illustrated in FIG. 3. In an embodiment, if the results provided by process 460 are not acceptable to the user after a predetermined number of cycles, a manual exposure mode is utilized.

Returning to FIG. 3, a focal plane for the passive reference image is acquired (314). According to embodiments of the present invention, the process described in steps 282-296 is utilized to perform step 314 by acquiring images of the passive reference. The new exposure time is utilized during the image acquisition process and the z-plane associated with the reaction chambers is determined. Accordingly, in an embodiment, after step 314, an appropriate exposure time and image capture plane are determined for subsequent acquisition of the reporter image.

An updated exposure time is optionally determined (316) in some embodiments. For purposes of determining the updated exposure time, the focal plane for the passive reference image is utilized and chamber pixels are considered during the image analysis process. The processes described in steps 460-470 are utilized to determine the updated exposure time, with the process proceeding to step 320 if the image is not saturated and the new exposure time is within the predetermined range. If the image is saturated or the new exposure time is out of range, a new image is acquired by returning the process to step 314 as indicated by process flow 318. In an embodiment, if the results provided by the iterative process flow 318 are not acceptable to the user after a predetermined number of cycles, a manual exposure mode is utilized.

An updated focal plane is optionally determined (320) as illustrated in FIG. 3. Determining an updated focal plane for the passive reference image includes repeating steps 314 and optional step 316 a number of times as appropriate to the particular application. This repetitive process is similar to the process described in steps 290-294 and is illustrated by process flow 322 in FIG. 3. Generally, the z-resolution of the process used in step 314 is increased (i.e., finer resolution) with each successive repetition. The results produced in this optional step are referred to as an updated focal plane for the passive reference image and an enhanced exposure time. It will be appreciated that the updated focal plane and the enhanced exposure time may be updated a number of times as process flow 322 is utilized.

The reporter images are acquired (324). These reporter images may include images including various reporter dyes such as FAM and VIC. These reporter images are acquired at either the focal plane determined in step 314 or the updated focal plane determined in step 320. Respective default exposure times are utilized in acquiring the images in step 324. In order to improve the image quality, the method of determining an exposure time for acquisition of a reporter image described in FIG. 4A or 4B are utilized in some embodiments. In an embodiment, only the chamber pixels are utilized in determining the exposure time as illustrated by method 460. Step 324 may be repeated several times as appropriate to the particular application, reacquiring the reporter images and determining updated exposure times. In an embodiment, if the results provided by process 324 are not acceptable to the user after a predetermined number of cycles, a manual exposure mode is utilized.

Figure 7A:
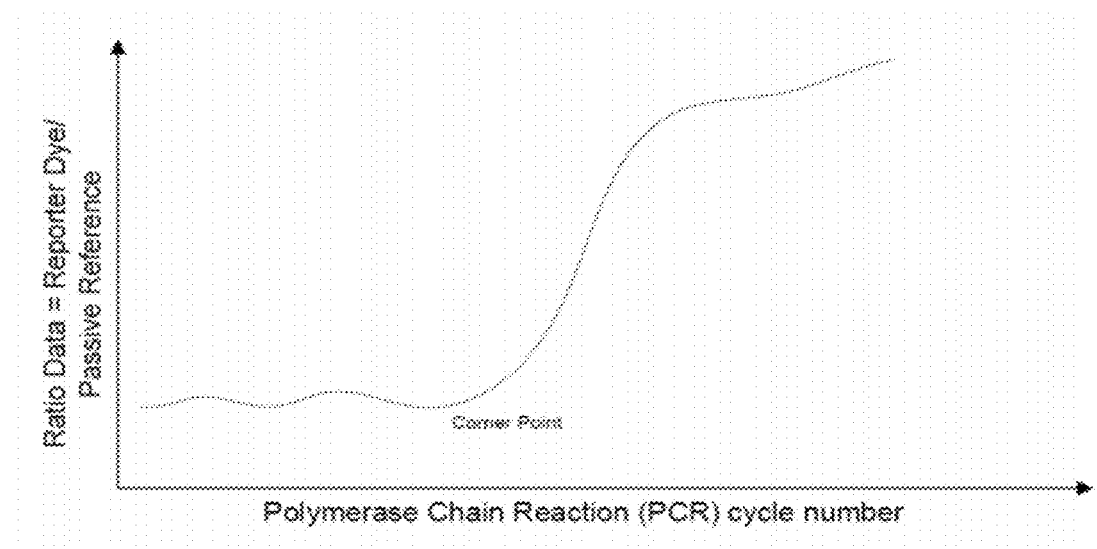
FIG. 7A-7D are simplified plots of PCR variables as a function of cycle number according to an embodiment of the present invention.

FIG. 7A-7D are simplified plots of PCR variables as a function of cycle number according to an embodiment of the present invention. According to embodiments of the present invention, techniques are provided to compute the corner point of ratio data curves. FIG. 7A is a simplified plot of the ratio of the reporter dye signal to the passive reference dye signal as a function of PCR cycle number (c). The data in FIG. 7A is associated with a single chamber and a single dye (e.g., FAM, or VIC). Such ratio data is referred to as RatioData in portions of the present specification. The Corner Point is illustrated as the cycle number at which the increase in the ratio begins to be noticeable in comparison with the noise level. As illustrated in FIG. 7A, the ratio data curve is associated with the DNA amplification curve, which can be approximated by:

$$\text{RatioData}[c] = K \cdot B^c, \tag{3}$$

where K is the original amount of DNA, B is the amplification factor, and c is the PCR cycle number. In an ideal experiment, the value of B=2. In practice, the measured value of the amplification factor B is less than two and represented by an approximate value (A), for example, A=1.9. For each cycle number c, the approximate value A of the amplification factor B is computed as the minimum of equation (4), (5) or (6):

$$\frac{\text{RatioData}[c+1] - \text{RatioData}[c-1]}{\text{RatioData}[c] - \text{RatioData}[c-2]} \tag{4}$$

$$\frac{\text{RatioData}[c+1]}{\text{RatioData}[c]} \tag{5}$$

$$\sqrt{\frac{\text{RatioData}[c+1]}{\text{RatioData}[c-1]}}. \tag{6}$$

Figure 7B:
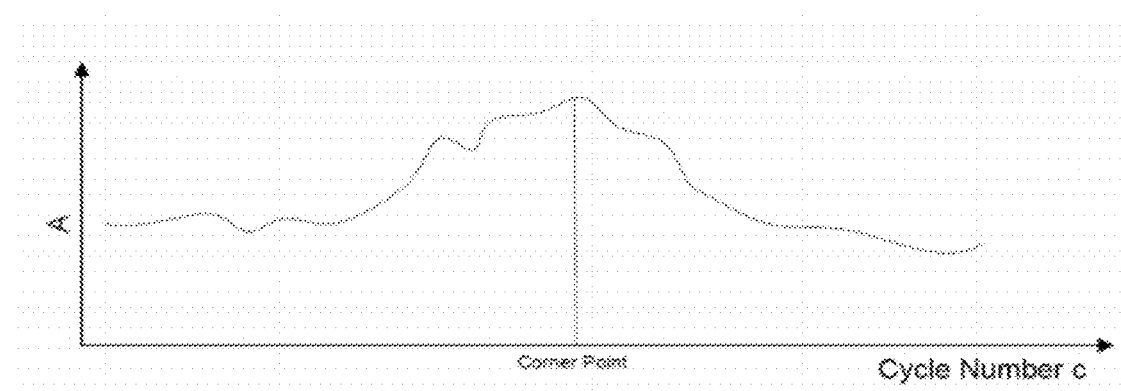

According to embodiments of the present invention, several methods are provided to determine the Corner Point given the RatioData plot. FIG. 7B is a simplified plot of the estimate A of the amplification factor for the RatioData illustrated in FIG. 7A. The plot of A is smoothed in some embodiments by applying a moving average filter. As will be appreciated, the value of A in an ideal experiment is equal to two and constant. Utilizing the plot illustrated in FIG. 7B, the amplification factor B is determined by finding the maximum value of A. In determining the maximum value of A, the cycles in which the RatioData is not monotonically increasing are ignored. As illustrated in FIG. 7B, the Corner Point is determined as the location of the maximum value of A.

Figure 7C:
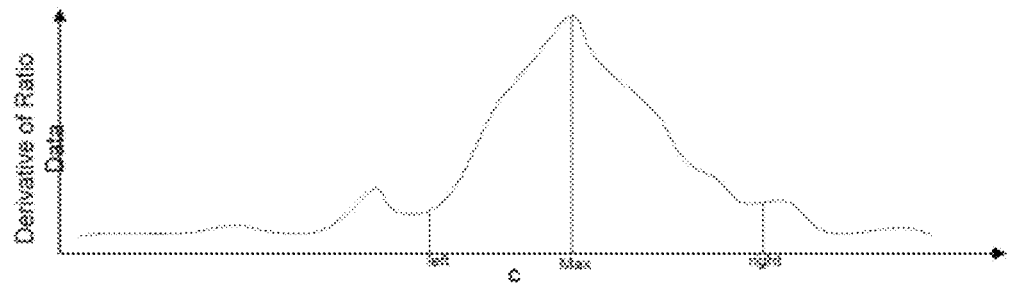

As an alternative to the method of determining the Corner Point described with respect to FIG. 7B, another method is illustrated in FIG. 7C. FIG. 7C is a simplified plot of the derivative of RatioData as a function of cycle number according to an embodiment of the present invention. In this alternative method, the maximum of the derivative of RatioData is determined. The cycle number marked "left" in FIG. 7C is determined by starting with the cycle number associated with the maximum derivative of RatioData (Max) and examining previous cycles until a cycle having a derivative less than or equal to a predetermined percentage of the value of the derivative at Max. In a particular embodiment, the predetermined percentage is 10%. In other embodiments, the percentage is greater than or less than 10% as appropriate to the particular applications. The cycle number marked "right" in FIG. 7C is determined in a similar manner. Starting with Max, subsequent cycles are examined to determine a cycle having a derivative less than or equal to the predetermined percentage. According to an embodiment, if the right and left cycle numbers are separated by at least six cycles and if the left cycle number is at least two cycles away from Max, then the left cycle number is identified as the Corner Point.

As another alternative to the methods of determining the Corner Point described with respect to FIGS. 7B and 7C, a third method is provided as follows. At each cycle c, two functions are fit using a window of several (e.g., 5) cycles. The first function (F) is a second order polynomial: $F = rx^2 + sx + t$, where r, s, and t are fitting coefficients. The second function (G) is an exponential curve: $G = A^x$, where A is the amplification factor previously computed for the given c. It will be appreciated that for a window of five cycles, x can take on the values of c, c+1, c+2, c+3, and c+4. The fitting error is defined as the sum of the squared differences between the fitted values and the actual values at a given cycle number. Using the notation above, ErrorF is the fitting error in fitting F and ErrorG is the fitting error in fitting G. The Corner Point is determined as the cycle number at which the difference in fitting errors (ErrorF−ErrorG) is a maximum.

In another embodiment, an alternative method to determine the Corner Point is provided. For purposes of clarity, this alternative method is referred to herein as the slope method. According to this alternative method, for each RatioData curve, the linear portion of the curve in log domain is determined. This is generally performed using a regression (line fitting) analysis. For each cycle number c, the longest possible straight line with a goodness-of-fit greater than 0.95 is fit to the RatioData curve in the log domain ($\log_2$). The Corner Point is determined by the cycle number which provides the maximum product of the length of the fitted line and the amplification factor at the given cycle number. In this computation, the amplification factor is the slope of the RatioData curve in the log domain. The amplification region is defined as the span of the fitted line associated with the Corner Point cycle number.

Figure 7D:
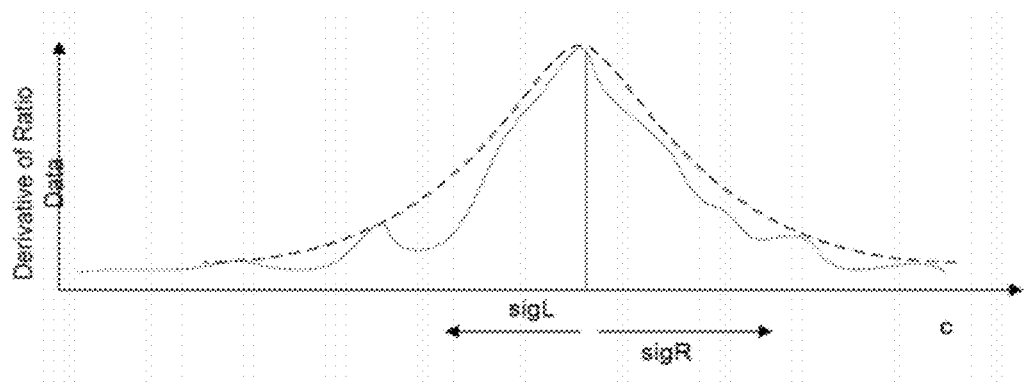

FIG. 7D is a simplified plot of the derivative of RatioData as a function of PCR cycle number. Embodiments of the present invention provide for quality measures that provide a metric to measure the properties of the amplification curve. As illustrated in FIG. 7D, an asymmetric fitting function (e.g., a Gaussian) is fit to the derivative of RatioData. Other functions other than a Gaussian are utilized in other embodiments as appropriate to the particular applications. Merely by way of example, other suitable fitting functions include derivative of Sigmoid, derivative of Hyperbolic Tangent, and the like. The fitting function is centered at the maximum of the derivative function and is asymmetric so that the standard deviation may be different for cycle numbers prior to (sigL) and after (sigR) the maximum derivative value.

A measure of the quality of the curve fit is provided by QualityG, which is the goodness-of-fit, a value that ranges between zero and one. In other embodiments, other ranges are provided as appropriate to the particular applications. Referring to the slope method described above, the slope of the fitted straight line associated with the Corner Point is assigned the value QualityS. An improved quality measure is provided by finding the minimum of the two values: QualityG and QualityS.

As illustrated in FIGS. 7A-7D, the RatioData values for a given reaction chamber are defined as equal to (ReporterDyeSignal−ReporterDyeBackground) divided by (ReferenceDyeSignal−ReferenceDyeBackground). In order to compute the background signal, an area in a surrounding neighborhood of a given reaction chamber is examined to determine the darkest (lowest intensity) value associated with the area. This examination is performed for both reporter dye images (e.g., FAM or VIC) as well as the reference dye images (e.g., ROX). The determined darkest values are then assigned the values of ReporterDyeBackground and ReferenceDyeBackground subtracted from the signals for the reaction chambers as shown in the equation above.

Figure 8:
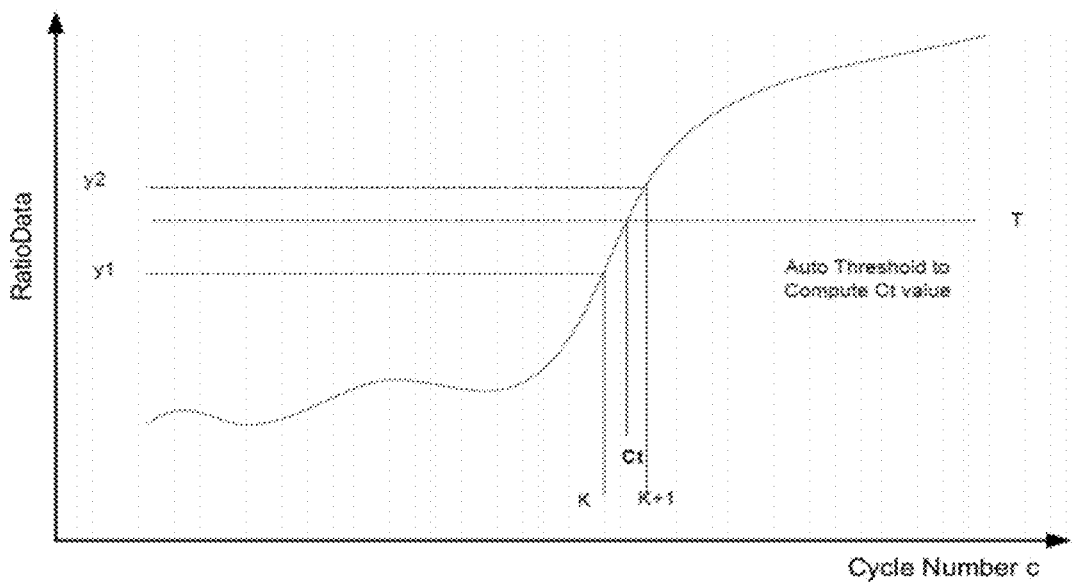
FIG. 8 is a simplified plot of a ratio data curve as a function of cycle number used in a threshold determination process according to an embodiment of the present invention.

FIG. 8 is a simplified plot of a ratio data curve as a function of cycle number used in a threshold determination process according to an embodiment of the present invention. In an embodiment, auto-thresholding is performed for a collection of amplification curves to determine the change in threshold (Ct) values. Referring to FIG. 8, for each RatioData curve, the linear portion of the curve in the log domain (also referred to as the exponential portion in the original data collection domain) is determined using regression analysis. For each cycle number c, the longest possible straight line in the log domain with a goodness-of-fit greater than 0.95 is determined. The Corner Point is determined as the cycle number that provides the maximum of the product of the length of the fitted straight line and the amplification factor (i.e., the slope of the fitted straight line) at the given cycle number. The span of the line is defined as the amplification region. A statistical parameter (e.g., the average) of the curve in the linear portion is used to determine the threshold for the given curve.

Examining the group of curves in succession, the thresholds for the various curves are considered. The overall average (or other statistical parameter) for the group of curves is used to determine the auto-threshold for the entire collection of amplification curves. The intersection of the amplification curve with the auto-threshold value is computed using the log graph and the following equation:

$$Ct = k + \frac{\log(T) - \log(y1)}{\log(y2) - \log(y1)}. \quad (7)$$

Figure 9A:
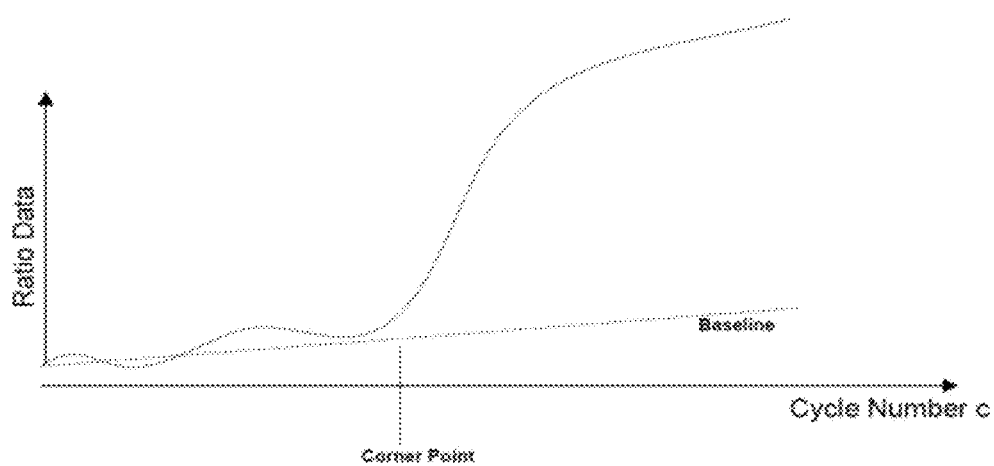
FIG. 9A is a simplified plot of the ratio data as a function of the number of PCR cycles according to an embodiment of the present invention.

Embodiments of the present invention provide methods and systems for baseline removal. In order to provide the final amplification curve, the baseline of the RatioData curve is subtracted from the ratio data. FIG. 9A is a simplified plot of the ratio data as a function of the number of PCR cycles according to an embodiment of the present invention. In an embodiment, the baseline is computed by determining a statistical measure (e.g., the average) of RatioData for the first N (e.g., 4) cycles. In another embodiment, N is determined as the minimum of either 4 or the cycle number associated with Corner Point. One of ordinary skill in the art would recognize many variations, modifications, and alternatives. Alternatively, a polynomial (e.g., a line as illustrated in FIG. 9A) may be fit to the first N points. Accordingly, the baseline is determined by one of several methods.

Figure 9B:
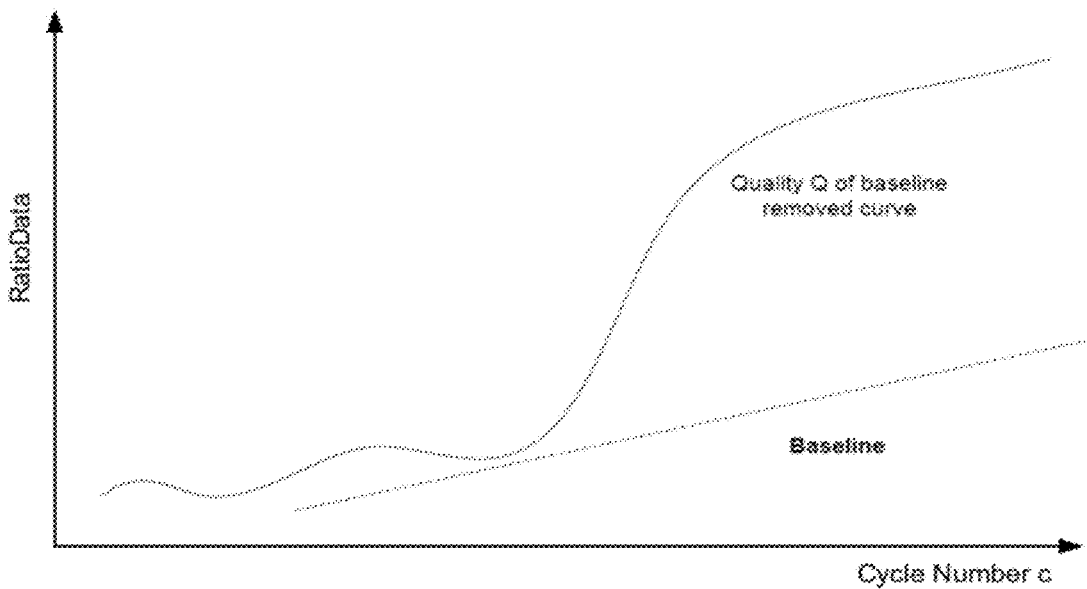
FIG. 9B is a simplified plot of the ratio data as a function of the number of PCR cycles according to an embodiment of the present invention.

FIG. 9B is a simplified plot of the ratio data as a function of the number of PCR cycles according to an embodiment of the present invention. In an embodiment, for all possible baselines characterized by a fitting error less than a predetermined value, the baseline removed curve with the best quality metric Q is selected as the baseline removed curve. As an example, a baseline could be determined using the methods described with respect to FIG. 9A. A range of baseline values are then selected based on (e.g., centered at) the determined baseline value. Utilizing this range of baseline values, the quality of a number of baseline removed curves are computed using the range of baseline values. The baseline removed curve with the best quality metric Q is determined and the particular baseline value utilized is determined as the baseline.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for an imaging system, the method comprising:
   providing a histogram of intensities of pixels of an image;
   computing an average intensity for a range of pixels; and
   computing an exposure time;
   computing a number of saturated pixels;
   determining that the exposure time is less than a predetermined time;

determining that the number of saturated pixels is less than a predetermined value; and utilizing the exposure time during an image acquisition process, wherein the image acquisition process images both chamber pixels and background pixels.

2. The method of claim 1 wherein the image is a passive reference image.

3. The method of claim 2 wherein the pixel intensities are associated with chamber pixels.

4. The method of claim 1 wherein the range of pixels runs from a first intensity value to a second intensity value.

5. A method of acquiring reporter images during a polymerase chain reaction (PCR) process, the method comprising:

acquiring a passive reference image;

determining an exposure time for the passive reference image;

determining a focal plane for the passive reference image; and acquiring a plurality of reporter images at the determined focal plane using the determined exposure time.

6. The method of claim 5 wherein the passive reference image includes one or more chambers containing a passive reference dye.

7. The method of claim 5 wherein determining an exposure time comprises:

providing a histogram of pixel intensities;

computing an average intensity for a range of pixels; and computing an exposure time;

computing a number of saturated pixels;

determining that the exposure time is less than a predetermined time; and determining that the number of saturated pixels is less than a predetermined value.

8. The method of claim 5 wherein the plurality of reporter images include one or more chambers containing a reporter dye.

9. The method of claim 8 wherein the plurality of reporter images are characterized by unsaturated emission from the reporter dye.

10. The method of claim 5 wherein determining a focal plane comprises:

acquiring an image stack comprising a plurality of images;

determining a focal plane characterized by a predetermined contrast score;

determining a plurality of positions associated with the plurality of chambers;

computing a contrast score for each of the plurality of images in the image stack; and determining an updated focal plane characterized by a second predetermined contrast score.

11. A method of determining a corner point for a polymerase chain reaction (PCR) ratio data curve, the method comprising:

a) computing an estimate of an amplification factor for a predetermined cycle number;

b) determining a fitting window for the PCR ratio data curve, wherein the fitting window is associated with the predetermined cycle number;

c) fitting a first function to the PCR ratio data curve over the fitting window;

d) determining a fitting error for the first function;

e) fitting a second function to the PCR ratio data curve over the fitting window f) determining a fitting error for the second function;

g) computing a difference between the fitting error for the first function and the fitting error for the second function, h) repeating steps a) through g) for subsequent cycle numbers; and i) identifying a maximum of the computed difference as the corner point.

12. The method of claim 11 wherein the first function comprises a second order polynomial.

13. The method of claim 11 wherein the second function comprises an exponential curve.

14. The method of claim 13 wherein the exponential curve is a function of the amplification factor.

15. The method of claim 11 wherein the fitting error comprises a sum of the squared differences between the fitted values and the actual values at a predetermined cycle number.

* * * * *